(12) United States Patent
Amrhein et al.

(10) Patent No.: US 8,974,806 B2
(45) Date of Patent: Mar. 10, 2015

(54) METHOD FOR PRODUCING AQUEOUS ACTIVE SUBSTANCE COMPOSITIONS OF ACTIVE SUBSTANCES THAT ARE HARDLY SOLUBLE IN WATER

(75) Inventors: Patrick Amrhein, Hochheim (DE); Holger Schöpke, Neckargemünd (DE); Gunnar Kleist, Baden-Baden (DE); Michael Kluge, Worms (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1710 days.

(21) Appl. No.: 11/658,472

(22) PCT Filed: Aug. 3, 2005

(86) PCT No.: PCT/EP2005/008430
§ 371 (c)(1),
(2), (4) Date: Jan. 25, 2007

(87) PCT Pub. No.: WO2006/015791
PCT Pub. Date: Feb. 16, 2006

(65) Prior Publication Data
US 2008/0213326 A1 Sep. 4, 2008

(30) Foreign Application Priority Data
Aug. 4, 2004 (DE) .................. 10 2004 037 850

(51) Int. Cl.
| | | |
|---|---|---|
| *A01N 25/12* | (2006.01) | |
| *A01P 15/00* | (2006.01) | |
| *A01P 3/00* | (2006.01) | |
| *A01P 13/00* | (2006.01) | |
| *A01N 43/36* | (2006.01) | |
| *A01N 25/04* | (2006.01) | |
| *A01N 25/26* | (2006.01) | |
| *A01N 25/28* | (2006.01) | |
| *A01N 43/653* | (2006.01) | |
| *A01N 53/00* | (2006.01) | |
| *C08L 97/02* | (2006.01) | |
| *B27K 3/00* | (2006.01) | |
| *B27K 3/15* | (2006.01) | |
| *C08L 33/08* | (2006.01) | |
| *C08L 35/02* | (2006.01) | |

(52) U.S. Cl.
CPC ............ *A01N 43/36* (2013.01); *A01N 25/04* (2013.01); *A01N 25/26* (2013.01); *A01N 25/28* (2013.01); *A01N 43/653* (2013.01); *A01N 53/00* (2013.01); *C08L 97/02* (2013.01); *B27K 3/007* (2013.01); *B27K 3/15* (2013.01); *C08L 33/08* (2013.01); *C08L 35/02* (2013.01)
USPC ........................................ 424/405; 424/489

(58) Field of Classification Search
CPC ......... C08L 97/20; C08L 33/08; C08L 35/02; B27K 3/007; B27K 3/15; A01N 25/04; A01N 25/26; A01N 25/28
See application file for complete search history.

(56) References Cited

U.S. PATENT DOCUMENTS

| | | |
|---|---|---|
| 3,400,093 A | 9/1968 | Feinberg |
| 2004/0138176 A1* | 7/2004 | Miles .............................. 514/65 |
| 2005/0255251 A1* | 11/2005 | Hodge et al. ................. 427/397 |

FOREIGN PATENT DOCUMENTS

| | | |
|---|---|---|
| CN | 1 491 541 A | 4/2004 |
| EP | 1 230 855 A1 | 8/2002 |
| FR | 1.598.644 A | 8/1970 |
| GB | 831790 A | 3/1960 |
| WO | WO-99/65301 A1 | 12/1999 |

(Continued)

OTHER PUBLICATIONS

Fenvalerate registry property data accessed via STN Dec. 12, 2008.*
Methylmethacrylate registry property data accessed via STN Dec. 12, 2008.*

(Continued)

*Primary Examiner* — Kortney L Klinkel
(74) *Attorney, Agent, or Firm* — Birch, Stewart, Kolasch & Birch, LLP

(57) ABSTRACT

The present invention relates to a process for preparing aqueous active compound compositions of active compounds which are poorly soluble in water, in particular of active compounds for the protection of crops and materials. Moreover, the invention relates to the active compound compositions obtainable by the process and to their use for controlling harmful organisms in plants and in the protection of materials.

The process comprises the following steps:
a) provision of an aqueous suspension of solid active compound particles of at least one active compound having a solubility in water of not more than 5 g/l at 25° C./1013 mbar, comprising, for stabilizing the active compound particles, at least one surfactant, where the active compound particles in the suspension have a mean particle size, determined by dynamic light scattering, of not more than 1200 nm,
b) emulsion polymerization of a first monomer composition M1 in the aqueous suspension of the active compound, where the monomer composition M1 comprises at least 95% by weight, based on its total weight, of at least one neutral, monoethylenically unsaturated monomer M1.1 having a solubility in water of not more than 30 g/l at 25° C./1013 mbar, giving an aqueous dispersion of polymer/active compound particles, and
c) emulsion polymerization of a second monomer composition M2 in an aqueous dispersion of the polymer/active compound particles obtained in step b), where the monomer composition M2 comprises at least 60% by weight, based on its total weight, of at least one neutral, monoethylenically unsaturated monomer M2.1 having a solubility in water of not more than 30 g/l at 25° C./1013 mbar.

20 Claims, No Drawings

(56) References Cited

FOREIGN PATENT DOCUMENTS

| | | |
|---|---|---|
| WO | WO-00/62612 A1 | 10/2000 |
| WO | WO-02/45507 A2 | 6/2002 |
| WO | WO-02/082900 A1 | 10/2002 |

OTHER PUBLICATIONS

Aoxystrobin registry property data accessed via STN Dec. 12, 2008.*
D.J. Shaw, Introduction to Colloid and Surface Chemistry, Butterworths, London, 1986, pp. 1-59.

* cited by examiner

… (US 8,974,806 B2)

METHOD FOR PRODUCING AQUEOUS ACTIVE SUBSTANCE COMPOSITIONS OF ACTIVE SUBSTANCES THAT ARE HARDLY SOLUBLE IN WATER

FIELD OF INVENTION

The present invention relates to a process for preparing aqueous active compound compositions of active compounds which are poorly soluble in water, in particular of active compounds for the protection of crops and materials. Moreover, the invention relates to the active compound compositions obtainable by the process and to their use for controlling harmful organisms in plants and in the protection of materials.

BACKGROUND OF THE INVENTION

Active compounds for crop protection and for the protection of materials, i.e. substances which, even at low concentration, may display physiological activity in the plant or in a harmful organism, for example insecticides, fungicides and herbicides, but also growth regulators, are frequently formulated and applied in the form of aqueous active compound preparations. Frequently, such formulations are aqueous concentrates which, prior to their application, are diluted by addition of a large amount of water to the desired application concentration (so-called "spray liquor").

A general problem in the case of aqueous active compound preparations is the generally poor solubility of the active compounds in water, which is frequently less than 5 g/l at 23° C./1013 mbar. Accordingly, aqueous formulations of such active compounds are heterogeneous systems where the active compound is present as an emulsified and/or dispersed phase in a continuous aqueous phase. For stabilizing these systems, which are metastable per se, it is customary to employ emulsifiers or dispersants. However, their stabilizing action is frequently unsatisfactory, so that the active compound may separate out, for example cream or sediment, in particular if the aqueous formulation is stored for a relatively long period of time at elevated temperature and/or at highly variable temperatures or close to freezing point. This problem is particularly pronounced if the active compound has a tendency to crystallize.

Organic solvents, too, are frequently used for preparing aqueous formulations of water-insoluble active compounds. Thus, water-miscible solvents are frequently used as solubilizers, i.e. to increase the solubility of the active compound in the aqueous phase. Water-immiscible solvents, in turn, serve to convert an active compound which is solid at the application temperature into a liquid phase which can then be emulsified. In contrast to the solid active compound, because of the solvent, the active compound is dissolved in the emulsion in molecular form and more readily available and more effective on application. However, owing to the known problems caused by VOC, the use of organic solvents is, for reasons related to work hygiene, because of environmental aspects and in some cases also for toxicological reasons, not desirable.

A further disadvantage of conventional aqueous active compound preparations is the relatively large particle size of the active compound particles and active compound droplets suspended and emulsified, respectively, in the aqueous phase, whose size is generally in the region of several μm. However, what is desired are aqueous formulations in which the active compound is present in the most highly dispersed form possible, firstly to ensure uniform distribution in the formulation and thus better handling and dosing properties and to increase simultaneously the bioavailability of the active compound in the formulation. What is desired here are formulations in which the mean particle sizes in the heterogeneous active compound-comprising phase are below 1500 nm, preferably below 1000 nm, in particular below 600 nm and especially below 300 nm.

There have been various proposals to formulate water-insoluble active compounds in the form of aqueous micro- or nanoemulsions (see, for example, WO 02/082900, WO 02/45507 and WO 99/65301). In contrast to conventional macroemulsions/suspensions which are usually milky/turbid and in which the particle sizes in the dispersed phase are significantly above 1 μm, the active compounds in the clear to opaque micro- or nanoemulsions are present in finely divided form, with particle sizes considerably below 1000 nm to up to 10 nm or below [see D. J. Shaw, Introduction to Colloid and Surface Chemistry, Butterworths, London 1986, p. 273]. However, the preparation of such micro- or nanoemulsions requires relatively large amounts of emulsifier and of organic solvents. However, the high proportion of emulsifiers does not only contribute to costs but can also lead to problems when applying the formulations. Solvents for their part are unwanted for reasons of work hygiene and for cost reasons. A further problem of such microemulsions is their instability with respect to breakdown.

Furthermore, there have been various descriptions of aqueous polymer/active compound preparations which are obtained by free-radical aqueous emulsion polymerization of a monomer emulsion, where the active compound is present in the monomer droplets of the monomer emulsion to be polymerized (see U.S. Pat. No. 3,400,093 and FR 1598644). However, this process is limited to active compounds which are readily soluble in the monomers. In general, these are substances which are liquid at room temperature.

SUMMARY OF THE INVENTION

Accordingly, it is an object of the present invention to provide aqueous preparations of active compounds which are insoluble or poorly soluble in water, in particular of active compounds for crop protection or for the protection of materials. These active compound compositions should be easy to prepare and should also be able to be formulated without any volatile organic substances or with only a very small content of volatile organic compounds. Furthermore desired is a high stability of the aqueous active compound compositions with respect to breakdown on prolonged storage and during dilution with water.

This object is achieved by a process which comprises the following steps:

a) provision of an aqueous suspension of solid active compound particles of at least one active compound having a solubility in water of not more than 5 g/l at 25° C./1013 mbar, comprising, for stabilizing the active compound particles, at least one surfactant, where the active compound particles in the suspension have a mean particle size, determined by dynamic light scattering, of not more than 1200 nm, b) emulsion polymerization of a first monomer composition M1 in the aqueous suspension of the active compound, where the monomer composition M1 comprises at least 95% by weight, based on its total weight, of at least one neutral, monoethylenically unsaturated monomer M1.1 having a solubility in water of not more than 30 g/l at 25° C./1013 mbar, giving an aqueous dispersion of polymer/active compound particles, and c) emulsion polymerization of a second monomer composition M2 in an aqueous dispersion of the polymer/active compound particles obtained in step b), where the monomer composition M2 comprises at least 60% by weight, based on its total weight, of at least one neutral, monoethylenically unsaturated monomer M2.1 having a solubility in water of not more than 30 g/l at 25° C./1013 mbar.

Accordingly, the present invention relates to the process described herein and to the aqueous active compound compositions obtainable by the process.

The aqueous active compound compositions obtained by the process according to the invention comprise the active compound in the form of finely divided suspended polymer/active compound particles, where the mean particle diameter of the polymer/active compound particles is generally below 1200 nm, frequently below 1000 nm, in particular below 600 nm and especially below 300 nm, for example in the range from 10 to 300 nm, preferably in the range from 20 to 250 nm and especially in the range from 30 to 200 nm. The stated particle sizes of the finely divided polymer are weight-average particle sizes which can be determined by dynamic light scattering. The person skilled in the art is familiar with methods to achieve this, for example from H. Wiese in D. Distler, Wässrige Polymerdispersionen [Aqueous Polymer Dispersions], Wiley-VCH 1999, chapter 4.2.1, p. 40 ff. and the literature cited therein, and also H. Auweter, D. Horn, J. Colloid Interf. Sci. 105 (1985) 399, D. Lilge, D. Horn, Colloid Polym. Sci. 269 (1991) 704 or H. Wiese, D. Horn, J. Chem. Phys. 94 (1991) 6429.

Active compounds in the context of this invention are generally, in principle, all substances causing a physiological reaction in an organism even at low concentration. The active compounds are preferably active compounds for crop protection and for the protection of materials, i.e. active compounds from the groups of the herbicides, fungicides, insecticides, acaricides, nematicides, bactericides, algicides, molluscicides, growth regulators and other biocides.

For the process according to the invention, it has been found to be advantageous if the active compound is present as a solid at a temperature of 40° C., in particular at 50° C., particularly preferably at 60° C., very particularly preferably at 70° C. and especially at 80° C., i.e. the active compound has a melting or decomposition point above 40° C., in particular above 50° C., particularly preferably above 60° C., very particularly preferably above 70° C. and especially above 80° C., for example in the range from 80 to 300° C. The active compound can be inorganic or organic.

DETAILED DESCRIPTION OF INVENTION

The person skilled in the art is familiar with suitable active compounds, for example from Ullmanns Encyclopedia of Industrial Chemistry, 5th ed. on CD-ROM, Wiley VCH 1997: chapter Fungicides, Insect Control and Weed Control, as from the Compendium of Pesticide Common Names, http://www.hclrss.demon.co.uk/index.html.

Suitable active compounds are in particular:
Herbicidally active compounds, in particular:
1,3,4-thiadiazoles, such as buthidazole and cyprazole;
amides, such as allidochlor, benzoylprop-ethyl, bromobutide, chlorthiamid, dimepiperate, dimethenamid, diphenamid, etobenzanid, flamprop, flamprop-methyl, fosamine, isoxaben, metazachlor, monalide, naptalam, pronamide, propanil, propyzamide, quinonamid;
aminotriazoles, such as amitrole,
anilides, such as anilofos, mefenacet, pentanochlor;
aryloxyalkanoic acids, such as 2,4-D, 2,4-DB, clomeprop, dichlorprop, dichlorprop-P, fenoprop, fluoroxypyr, MCPA, MCPB, mecoprop, mecoprop-P, napropamide, napropanilide, triclopyr;
benzoic acids, such as chloramben, dicamba;
benzothiadiazinones, such as bentazone;
bleachers, such as clomazone, diflufenican, fluorochloridone, flupoxam, fluridone, karbutilate, pyrazolate, sulcotrione, mesotrione;
carbamates, such as asulam, carbetamide, chlorbufam, chlorpropham, desmedipham, phenmedipham, vernolate;
quinolinic acids, such as quinclorac, quinmerac;
dichloropropionic acids, such as dalapon;
dihydrobenzofurans, such as ethofumesate;
dihydrofuran-3-ones, such as flurtamone;
dinitroanilines, such as benefin, butralin, dinitramine, ethalfluralin, fluchloralin, isopropalin, nitralin, oryzalin, pendimethalin, prodiamine, profluralin, trifluralin;
dinitrophenols, such as bromofenoxim, dinoseb, dinoseb-acetate, dinoterb, DNOC, minoterb-acetate;
diphenyl ethers, such as acifluorofen, acifluorfen-sodium, aclonifen, bifenox, chlornitrofen, difenoxuran, ethoxyfen, fluorodifen, fluoroglycofen-ethyl, fomesafen, furyloxyfen, lactofen, nitrofen, nitrofluorfen, oxyfluorfen;
ureas, such as benzthiazuron, DCU, diflufenzopyr, methabenzthiazuron;
imidazolinones, such as imazamethapyr, imazapyr, imazaquin, imazethabenz-methyl, imazethapyr, imazapic, imazamox;
oxadiazoles, such as methazole, oxadiargyl, oxadiazon;
oxiranes, such as tridiphane;
phenols, such as bromoxynil, ioxynil;
phenoxyphenoxypropionic acid esters, such as clodinafop, cyhalofop-butyl, diclofop-methyl, fenoxaprop-ethyl, fenoxaprop-p-ethyl, fenthiaprop-ethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl;
phenylacetic acids, such as chlorfenac;
phenylureas, such as buturon, chlorotoluron, chlorbromuron, chloroxuron, dimefuron, diuron, fenuron, isoproturon, linuron, monolinuron, monuron, metobenzuron, metobromuron, metoxuron, neburon;
phenylpropionic acids, such as chlorophenprop-methyl;
ppi-active compounds, such as benzofenap, flumichlorac, flumiclorac-pentyl, flumioxazin, flumipropyn, fluropacil, pyrazoxyfen, sulfentrazone, thidiazimin;
pyrazoles, such as nipyraclofen;
pyridazines, such as chloridazon, maleic hydrazide, norflurazon, pyridate;
pyridinecarboxylic acids, such as clopyralid, dithiopyr, picloram, thiazopyr;
pyrimidyl ethers, such as pyrithiobac-acid, pyrithiobac-sodium, KIH-2023, KIH-6127;
sulfonamides, such as flumetsulam, metosulam;
sulfonylureas, such as amidosulfuron, azimsulfuron, bensulfuron-methyl, chlorimuron-ethyl, chlorsulfuron, cinosulfuron, cyclosulfamuron, ethoxysulfuron, ethametsulfuron-methyl, flazasulfuron, flupyrsulfuron-methyl, foramsulfuron, halosulfuron-methyl, imazosulfuron, idosulfuron, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl, tritosulfuron;

thiadiazolylureas, such as ethidimuron, tebuthiuron, thiazafluoron;

triazines, such as ametryn, atrazine, atraton, cyanazine, cyprazine, desmetryn, dipropetryn, isomethiozin, propazine, promethryn, prometon, sebuthylazine, secbumethon, simazine, tebutryn, terbumeton, terbuthylazine, trietazine;

triazolecarboxamides, such as triazofenamide;

uracils, such as bromacil, butafenacil, lenacil, terbacil;

furthermore azafenidin, aziprotryne, bromuron, benazolin, benfuresate, bensulide, benzofluor, bentazon, bromofenoxim, butamifos, cafenstrole, chlorthal-dimethyl, cinmethylin, cinidon-ethyl, defenuron, dichlobenil, endothall, fluorbentranil, fluthiacet-methyl, inxynil, isoxaflutole, mefluidide, methazole, metribuzin, metramitron, perfluidone, piperophos, topramezone;

crop protection agents of the cyclohexenone type, such as alloxydim, clethodim, cloproxydim, cycloxydim, sethoxydim and tralkoxydim. Very particularly preferred herbicidally active compounds of the cyclohexenone type are: tepraloxydim (cf. AGROW, No. 243, 11.3.95, page 21, caloxydim) and 2-(1-[2-{4-chlorophenoxy}propyloxyimino]butyl)-3-hydroxy-5-(2H-tetrahydrothiopyran-3-yl)-2-cyclohexen-1-one, and a very particularly preferred herbicidally active compound of the sulfonylurea type is: N-(((4-methoxy-6-[trifluoromethyl]-1,3,5-triazin-2-yl)amino)-carbonyl)-2-(trifluoromethyl)benzenesulfonamide;

Fungicidally active compounds, in particular:

acylalanines, such as benalaxyl, metalaxyl, ofurace, oxadixyl;

amine derivatives, such as aldimorph, dodine, dodemorph, fenpropimorph, fenpropidin, guazatine, iminoctadine, spiroxamine, tridemorph;

anilinopyrimidines, such as pyrimethanil, mepanipyrim or cyprodinil;

antibiotics, such as cycloheximide, griseofulvin, kasugamycin, natamycin, polyoxin and streptomycin;

azoles: azaconazole, bitertanol, bromoconazole, cyproconazole, dichlobutrazole, difenoconazole, dinitroconazole, epoxiconazole, fenbuconazole, fluquinconazole, flusilazole, flutriafol, ketoconazole, hexaconazole, metconazole, myclobutanil, penconazole, propiconazole, prothioconazole, tebuconazole, tetraconazole, triadimefon, triadimenol, triflumizole, triticonazole;

dicarboximides, such as iprodione, myclozolin, procymidone, vinclozolin;

dithiocarbamates: ferbam, nabam, maneb, mancozeb, metam, metiram, propineb, polycarbamate, thiram, ziram, zineb;

heterocyclic compounds, such as anilazine, benomyl, boscalid, carbendazim, carboxin, oxycarboxin, cyazofamid, dazomet, dithianon, famoxadone, fenamidone, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamide, thiophenate-methyl, tiadinil, tricyclazole, triforine;

nitrophenyl derivatives, such as binapacryl, dinocap, dinobuton, nitrophthal-isopropyl;

phenylpyrroles, such as fenpiclonil and also fludioxonil;

2-methoxybenzophenones as described in EP-A 897904 by the general formula I, for example metrafenone;

fungicides not belonging to any of the other classes, such as acibenzolar-S-methyl, benthiavalicarb, carpropamid, chlorothalonil, cyflufenamid, cymoxanil, diclomezine, diclocymet, diethofencarb, edifenphos, ethaboxam, fenhexamid, fentin-acetate, fenoxanil, ferimzone, fluazinam, fosetyl, foestyl-aluminum, iprovalicarb, hexachlorobenzol, pencycuron, propamocarb, phthalide, toloclofos-methyl, quintozene, zoxamide;

strobilurins as described in WO 03/075663 by the general formula I, for example: azoxystrobin, dimoxystrobin, fluoxastrobin, kresoxim-methyl, metominostrobin, orysastrobin, picoxystrobin, pyraclostrobin and trifloxystrobin;

sulfenic acid derivatives, such as captafol, captan, dichlofluanid, folpet, tolylfluanid;

cinnamides and analogs thereof, such as dimethomorph, flumetover, flumorph;

6-aryl-[1,2,4]triazolo[1,5-a]pyrimidines as described, for example, in WO 98/46608, WO 99/41255 or WO 03/004465 in each case by the general formula I, for example 5-chloro-7-(4-methylpiperidin-1-yl)-6-(2,4,6-trifluorophenyl)-[1,2,4]triazolo-[1,5-a]pyrimidine, 5-chloro-7-(4-methylpiperazin-1-yl)-6-(2,4,6-trifluorophenyl)-[1,2,4]triazolo[1,5-a]pyrimidine, 5-chloro-7-(piperidin-1-yl)-6-(2,4,6-trifluorophenyl)-[1,2,4]triazolo[1,5-a]pyrimidine, 5-chloro-7-(morpholin-1-yl)-6-(2,4,6-trifluorophenyl)-[1,2,4]triazolo[1,5-a]pyrimidine, 5-chloro-7-(isopropylamino)-6-(2,4,6-trifluorophenyl)-[1,2,4]triazolo[1,5-a]pyrimidine, 5-chloro-7-(cyclopentylamino)-6-(2,4,6-trifluorophenyl)-[1,2,4]triazolo[1,5-a]pyrimidine, 5-chloro-7-(2,2,2-trifluoroethylamino)-6-(2,4,6-trifluorophenyl)-[1,2,4]triazolo[1,5-a]-pyrimidine, 5-chloro-7-(1,1,1-trifluoropropan-2-ylamino)-6-(2,4,6-trifluorophenyl)-[1,2,4]triazolo[1,5-a]pyrimidine, 5-chloro-7-(3,3-dimethylbutan-2-ylamino)-6-(2,4,6-trifluorophenyl)-[1,2,4]triazolo[1,5-a]pyrimidine, 5-chloro-7-(cyclohexylmethyl)-6-(2,4,6-trifluorophenyl)-[1,2,4]triazolo[1,5-a]pyrimidine, 5-chloro-7-(cyclohexyl)-6-(2,4,6-trifluorophenyl)-[1,2,4]triazolo[1,5-a]pyrimidine, 5-chloro-7-(2-methylbutan-3-yl)-6-(2,4,6-trifluorophenyl)-[1,2,4]triazolo[1,5-a]pyrimidine, 5-chloro-7-(3-methylpropan-1-yl)-6-(2,4,6-trifluorophenyl)-[1,2,4]triazolo[1,5-a]-pyrimidine, 5-chloro-7-(4-methylcyclohexan-1-yl)-6-(2,4,6-trifluorophenyl)-[1,2,4]triazolo[1,5-a]pyrimidine, 5-chloro-7-(hexan-3-yl)-6-(2,4,6-trifluorophenyl)-[1,2,4]triazolo[1,5-a]pyrimidine, 5-chloro-7-(2-methylbutan-1-yl)-6-(2,4,6-trifluorophenyl)-[1,2,4]triazolo[1,5-a]pyrimidine, 5-chloro-7-(3-methylbutan-1-yl)-6-(2,4,6-t-fluorophenyl)-[1,2,4]triazolo[1,5-a]pyrimidine, 5-chloro-7-(1-methylpropan-7-(yl)-6-(2,4,6-trifluorophenyl)-[1,2,4]triazolo[1,5-a]pyrimidine, 5-methyl-7-(4-methylpiperidin-1-yl)-6-[((2,4,6-trifluorophenyl)-[1,2,4]triazolo, 5-a]pyrimidine, 5-methyl-7-(4-methylpiperazin-1-yl)-6-(2,4,6-trifluorophenyl)-[1,2,4]triazolo[1,5-a]pyrimidine, 5-methyl-7-(morpholin-1-yl)-6-(2,4,6-trifluorophenyl)-[1,2,4]triazolo[1,5-a]pyrimidine, 5-methyl-7-(piperidin-1-yl)-6-(2,4,6-trifluorophenyl)-[1,2,4]triazolo-[1,5-a]pyrimidine, 5-methyl-7-(isopropylamino)-6-(2,4,6-trifluorophenyl)-[1,2,4]triazolo[1,5-a]pyrimidine, 5-methyl-7-(cyclopentylamino)-6-(2,4,6-trifluorophenyl)-[1,2,4]triazolo[1,5-a]pyrimidine, 5-methyl-7-(2,2,2-trifluorethylamino)-6-(2,4,6-trifluorophenyl)-[1,2,4]triazolo[1,5-a]pyrimidine, 5-methyl-7-(1,1,1-trifluoropropan-2-ylamino)-6-(2,4,6-trifluorophenyl)-[1,2,4]triazolo[1,5-a]pyrimidine, 5-methyl-7-(3,3-dimethylbutan-2-ylamino)-6-(2,4,6-trifluorophenyl)-[1,2,4]triazolo-[1,5-a]pyrimidine, 5-methyl-7-(cyclohexylmethyl)-6-(2,4,6-trifluorophenyl)-[1,2,4]-triazolo[1,5-a]pyrimidine, 5-methyl-7-(cyclohexyl)-6-(2,4,6-trifluorophenyl)-[1,2,4]-triazolo[1,5-a]pyrimidine, 5-methyl-7-(2-methylbutan-3-yl)-6-(2,4,6-trifluorophenyl)-[1,2,4]triazolo[1,5-a]pyrimidine, 5-methyl-7-(3-methylpropan-1-yl)-6-(2,4,6-trifluorophenyl)-[1,2,4]triazolo[1,5-a]pyrimidine, 5-methyl-7-(4-methylcyclohexan-1-yl)-6-(2,4,6-trifluorophenyl)-[1,2,4]triazolo[1,5-a]pyrimidine, 5-methyl-7-(hexan-3-yl)-6-(2,4,6-trifluorophenyl)-[1,2,4]triazolo[1,5-a]pyrimidine, 5-methyl-7-(2-methylbutan-1-yl)-6-(2,4,6-trifluorophenyl)-[1,2,4]triazolo[1,5-a]pyrimidine, 5-methyl-7-(3-methylbutan-1-yl)-6-(2,4,6-trifluorophenyl)-[1,2,4]triazolo[1,5-a]pyrimidine and 5-methyl-7-(1-methylpropan-1-yl)-6-(2,4,6-trifluorophenyl)-[1,2,4]triazolo[1,5-a]-pyrimidine;

amide fungicides, such as cycloflufenamid, and also (Z)—N-[α-(cyclopropylmethoxy-imino)-2,3-difluoro-6-(difluoromethoxy)benzyl]-2-phenylacetamide;

Insecticides, in particular:

organophosphates, such as azinphos-methyl, azinphos-ethyl, chlorpyrifos, chlorpyrifos-methyl, chlorfenvinphos, diazinon, dimethylvinphos, dioxabenzofos, disulfoton, ethion, EPN, fenitrothion, fenthion, heptenophos, isoxathion, malathion, methidathion, methyl-parathion, paraoxon, parathion, phenthoate, phosalone, phosmet, phorate, phoxim, pirimiphos-methyl, profenofos, prothiofos, primiphos-ethyl, pyraclofos, pyridaphenthion, sulprofos, triazophos, trichlorfon, tetrachlorvinphos, vamidothion;

carbamates, such as alanycarb, benfuracarb, bendiocarb, carbaryl, carbofuran, carbosulfan, fenoxycarb, furathiocarb, indoxacarb, methiocarb, pirimicarb, propoxur, thiodicarb, triazamate;

pyrethroids, such as acrinathrin, allethrin, bioallethrin, barthrin, bioethanomethrin, cyclethrin, bifenthrin, cyfluthrin, beta-cyfluthrin, cycloprothrin, cypermethrin, cyphenothrin, deltamethrin, dimefluthrin, dimethrin, empenthrin, esfenvalerate, etofenprox, flufenprox, halfenprox, protifenbute, fenpirithrin, fenfluthrin, fenpropathrin, fenvalerate, flucythrinate, furethrin, imiprothrin, metofluthrin, cyhalothrin, lambda-cyhalothrin, gamma-cyhalothrin, permethrin, biopermethrin, transpermethrin, phenothrin, prallethrin, profluthrin, pyresmethrin, resmethrin, bioresmethrin, cismethrin, silafluofen, fluvalinate, tau-fluvalinate, tefluthrin, terallethrin, tetramethrin, tralomethrin, alpha-cypermethrin, beta-cypermethrin, theta-cypermethrin, zeta-cypermethrin, permethrin;

arthropod growth regulators: a) chitin synthesis inhibitors, for example benzoylureas, such as chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists, such as halofenozide, methoxyfenozide, tebufenozide; c) juvenoids, such as pyriproxyfen, methoprene; d) lipid biosynthesis inhibitors, such as spirodiclofen;

neonicotinoids, such as flonicamid, clothianidin, dinotefuran, imidacloprid, thiamethoxam, nithiazine, acetamiprid, thiacloprid;

further unclassified insecticides, such as abamectin, acequinocyl, acetamiprid, amitraz, azadirachtin, bensultap, bifenazate, cartap, chlorfenapyr, chlordimeform, diafenthiuron, dinetofuran, diofenolan, emamectin, endosulfan, ethiprole, fenazaquin, fipronil, formetanate, formetanate hydrochloride, gamma-HCH, hydramethylnon, imidacloprid, indoxacarb, isoprocarb, metolcarb, pyridaben, pymetrozine, spinosad, tebufenpyrad, thiamethoxam, thiocyclam, pyridalyl, flonicamid, fluacypyrim, milbemectin, spiromesifen, flupyrazofos, NC 512, tolfenpyrad, flubendiamide, bistrifluoron, benclothiaz, pyrafluprole, pyriprole, amidoflumet, flufenerim, cyflumetofen, acequinocyl, lepimectin, profluthrin, dimefluthrin, XMC and xylylcarb and compounds of the formula below

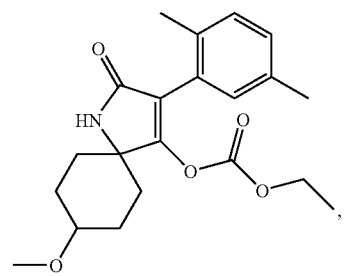 [SMILES: CCOC(=O)OC1=C(c2cc(C)ccc2C)C(=O)NC12CCC(OC)CC2 ; ","]

aminoisothiazoles of the formula

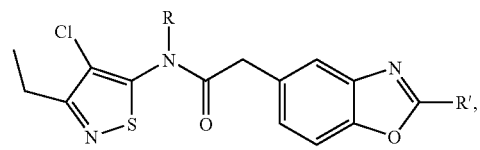

in which
R is CH$_2$O—CH$_3$ or H and
R' is CF$_2$CF$_2$CF$_3$;
anthranilamides of the formula

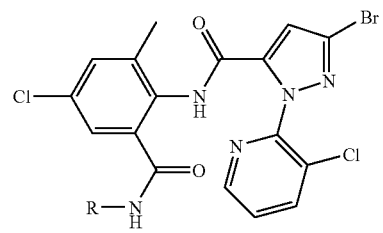

in which R is C$_1$-C$_4$-alkyl, such as methyl, ethyl, isopropyl or n-butyl,
compounds of the formulae below

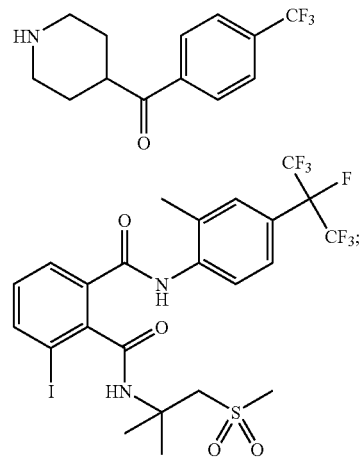

furthermore
N-phenylsemicarbazones as described in EP-A 462 456 by the formula I, in particular compounds of the general formula IV

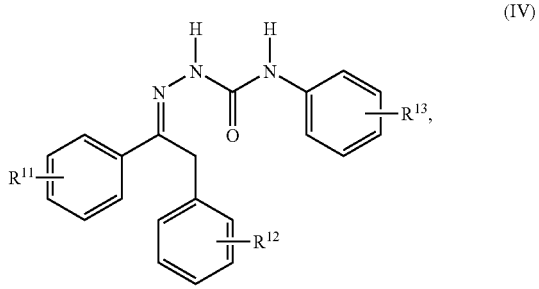

(IV)

in which $R^{11}$ and $R^{12}$ independently of one another are hydrogen, halogen, CN, $C_1$-$C_4$-alkyl, $C_1$-$C_4$-alkoxy, $C_1$-$C_4$-haloalkyl or $C_1$-$C_4$-haloalkoxy and $R^{13}$ is $C_1$-$C_4$-alkoxy, $C_1$-$C_4$-haloalkyl or $C_1$-$C_4$-haloalkoxy, for example compound IV in which $R^{11}$ is 3-$CF_3$ and $R^{12}$ is 4-CN and $R^{13}$ is 4-$OCF_3$ (=metaflumizone);

acaricides, in particular bromopropylate, spirodiclofen, clofentezine, fenpyroximate, hexythiazox;

growth regulators, for example ancymidol, azoluron, chlorflurenol-methyl, flurprimidol, forchlorfenuron, indolylbutyric acid, mefluidide, 1-naphthylacetamide, 1-naphthylacetic acid, 2-naphthyloxyacetic acid (ester), paclobutrazol, thidiazuron, 3-CPA, 4-CPA, BAP, butifos, tribufos, butralin, chlorflurenol, clofencet, cyclanilide, daminozide, dicamba, dikegulac sodium, dimethipin, chlorfenethol, etacelasil, ethephon, ethychlozate, fenoprop, 2,4,5-TP, fluoridamid, flurprimidol, flutriafol, guazatin, imazalil, karetazan, kinetin, lactidichlor-ethyl, maleic hydrazide, naptalam, quinmerac, sintofen, tetcyclacis, triiodobenzoic acid, triapenthenol, triazethan, tribufos, trinexapac-ethyl, uniconazole, propham and gibberillic acid and gibberellins. The latter include, for example, the gibberellins $GA_1$, $GA_3$, $GA_4$, $GA_5$ and $GA_7$ etc. and the corresponding exo-16,17-dihydrogibberellins and derivatives thereof, for example the esters with $C_1$-$C_4$-carboxylic acids;

bactericides, in particular 1,2-benzisothiazol-3(2H)-one (BIT), carbendazim, chlorotoluron, mixtures of 5-chloro-2-methyl-4-isothiazolin-3-one with 2-methyl-4-isothiazolin-3-one, 2,2-dibromo-3-nitrilopropionamide (DBNPA), fluometuron, 3-iodo-2-propynylbutyl carbamate (IPBC), isoproturon, 2-n-octyl-4-isothiazolin-3-one (OIT), prometryn, propiconazole;

algicides, in particular quinoclamine and quinonamid;

bactericides, such as 2-phenylphenol, thymol, 4-tert-amylphenol, 4-chloro-3-methylphenol, 4-chloro-2-benzylphenol and 4-chloro-3,5-dimethylphenol; and molluscicides, such as clonitralid.

Active compounds which are preferred for preparing active compound compositions according to the process according to the invention are selected from the group consisting of conazole fungicides, strobilurins, pyrethroids and arylpyrrole insecticides. Preference is likewise given to compositions according to the invention which comprise one of the 6-aryl-[1,2,4]triazolo[1,5-a]pyrimidines described above.

In general, the solid active compound, which may be amorphous, crystalline or semicrystalline and which is preferably already present in particulate form, for example as a powder, as crystals, as a granulate or as a comminuted solidified melt, is used to prepare the aqueous suspension of solid active compound particles. The particles of the solid active compound may be of regular or irregular shape. For example, the active compound particles can be present in spherical or virtually spherical form or in the form of needles. It is, of course, also possible to use mixtures of different active compounds.

To prepare the aqueous suspension of the active compound particles, the solid active compound is comminuted, preferably ground, in a manner known per se to the desired particle size.

Commination is carried out in apparatus suitable for this purpose, preferably in mills, such as, for example, ball mills, agitator ball mills, circulating mills (agitator ball mills with pin grinding system), disk mills, annular chamber mills, double cone mills, triple roll mills and batch mills. To dissipate the heat energy introduced during the grinding process, the grinding chambers are preferably fitted with cooling systems.

Comminution is preferably carried out by wet grinding, i.e. commination is carried out with addition of an inert liquid, preferably in the presence of a partial amount, with preference the major amount, in particular at least 80%-100% of the surfactant, and also, if appropriate, in the presence of water and/or an organic solvent not capable of dissolving the active compound. Apparatus suitable for wet grinding are known. These include, in particular, the abovementioned mills and triple roll mills. Particularly suitable is the ball mill Drais Superflow DCP SF 12, the circulating mill system ZETA from Netzsch-Feinmahltechnik GmbH or the disk mill from Netzsch Feinmahltechnik GmbH, Selb, Germany.

Comminution is preferably carried out in a manner such that the mean diameter of the active compound particles after commination is in the range from 20 nm to 1.2 μm, preferably in the range from 20 to 1000 nm, in particular in the range from 30 to 800 nm, particularly preferably in the range from 40 to 500 nm and very particularly preferably in the range from 50 to 200 nm. As a result of aggregation processes, particle sizes in the range from 300 to 1200 nm and in particular in the range from 500 to 1000 nm are frequently observed after the grinding process has been completed. However, in general, the actual commination grade is much higher, i.e. the primary particle size of the aggregated active compound particles is much smaller and is in the ranges given above as being particularly preferred or very particularly preferred. This is easily established by the person skilled in the art by carrying out the polymerization steps of the process according to the invention in which these aggregates are broken up, so that the particle sizes obtained during polymerization reflect the particle sizes achieved during commination. Using a few standard tests, the person skilled in the art is generally capable to establish the conditions of the commination process required to achieve the desired particle size of the active compound particles.

The time required for commination depends in a manner known per se on the desired grade of fineness or the desired particle size of the active compound particle and can be determined by the person skilled in the art in standard experiments. Grinding times of, for example, in the range from half an hour to 48 hours have been found to be suitable, although a longer period of time is also conceivable. A commination time of 5 to 24 hours is preferred.

The pressure and temperature conditions during commination are generally not critical; thus, for example, atmospheric pressure has been found to be suitable. Temperatures of, for example, in the range from 10° C. to 100° C. have been found to be suitable temperatures; the chosen temperatures are usually temperatures at which the active compound is present as a solid.

According to the invention, the aqueous suspension, provided in step a), of the active compound particles comprises at least one surfactant to stabilize the active compound particles.

The surfactant may be added during commination of the active compound particles or subsequently thereto. Preferably, prior to commination the active compound is mixed with the major amount, preferably with at least 80% and in particular with the total amount of the surfactant comprised in the aqueous suspension of the active compound particles.

The surfactant is preferably a nonionic surfactant. However, ionic surfactants and mixtures of nonionic surfactants with ionic surfactants are also suitable, the proportion of nonionic surfactants in the mixture being preferably at least 50% by weight, in particular from 70 to 99% by weight. The weight ratio of active compound to surfactant can be chosen from a wide range and is generally in the range from 50:1 to 1:2, preferably in the range from 20:1 to 1:1 and in particular in the range from 10:1 to 1.3:1.

Examples of suitable nonionic surfactants are, for example, ethoxylated mono-, di- and trialkylphenols (degree of ethoxylation: 3 to 50, alkyl radical: $C_3$-$C_{12}$) and ethoxylated fatty alcohols (degree of ethoxylation: 3 to 80; alkyl radical: $C_8$-$C_{36}$). Examples of these are the Lutensol® brands of BASF AG or the Triton® brands of Union Carbide. Particularly preferred are ethoxylated straight-chain fatty alcohols of the formula

$n$-$C_xH_{2x+1}$—$O(CH_2CH_2O)_y$—H, where x are integers in the range from 10 to 24, preferably in the range from 12 to 20. The variable y is preferably an integer in the range from 5 to 50, particularly preferably 8 to 40. Ethoxylated straight-chain fatty alcohols are usually present as a mixture of various ethoxylated fatty alcohols having a different degree of ethoxylation. In the context of the present invention the variable y denotes the mean (number average). Other suitable nonionic surfactants are copolymers, in particular block copolymers of ethylene oxide and at least one $C_3$-$C_{10}$-alkylene oxide, for example triblock copolymers of the formula

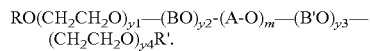

$RO(CH_2CH_2O)_{y1}$—$(BO)_{y2}$-$(A$-$O)_m$—$(B'O)_{y3}$—$(CH_2CH_2O)_{y4}R'$.

in which m is 0 or 1, A is a radical derived from an aliphatic, cycloaliphatic or aromatic diol, for example ethane-1,2-diyl, propane-1,3-diyl, butane-1,4-diyl, cyclohexane-1,4-diyl, cyclohexane-1,2-diyl or bis(cyclohexyl)methane-4,4'-diyl, B and B' independently of one another are propane-1,2-diyl, butane-1,2-diyl or phenylethane-1,2-diyl, R and R' are hydrogen or $C_1$-$C_{10}$-alkyl, y1 and y4 independently of one another are a number from 2 to 100 and y2, y3 independently of one another are a number from 2 to 100, where the sum y1+y2+y3+y4 is preferably in the range from 20 to 400, which corresponds to a number-average molecular weight in the range from 1000 to 20 000. A is preferably ethane-1,2-diyl, propane-1,3-diyl or butane-1,4-diyl. B is preferably propane-1,2-diyl.

Suitable ionic surfactants are the anionic and cationic emulsifiers and protective colloids mentioned below in connection with step b) or step c).

During commination, water may be added. The amount of water is preferably from 0.5 to 5 parts by weight, based on 1 part by weight of the active compound. It is also possible to add customary nonionic grinding auxiliaries.

In one variant, the active compound is comminuted in the presence of nanoparticular silica. Nanoparticular silica is silica having an average particle size <100 nm, for example in the range from 1 to 100 nm and in particular in the range from 5 to 50 nm. Here, the nanoparticular silica is preferably employed in an amount of from 1 to 50% by weight, based on the active compound to be comminuted. The silica is usually employed in the form of an aqueous dispersion which generally has a solids content of from 5 to 50% by weight and in particular from 10 to 40% by weight of silica, based on the total weight of the dispersion. The use of nanoparticular silica results in an improved stabilization of the active compound particles by preventing agglomerization of the active compound particles and, by virtue of its abrasive action, it also enhances the process of division. Nanoparticular silica, in particular aqueous dispersions of nanoparticular silica, are known to the person skilled in the art and commercially available, for example under the name Köstrosol® 0830 from Chemiewerk Bad Köstritz GmbH.

The resulting comminuted active compound particles are subsequently suspended in an aqueous medium, which yields an aqueous suspension of the active compound particles. For dispersion, it is possible to use any apparatus which promote mixing of the active compound particles with the aqueous medium, for example stirred vessel ultrasound homogenizers, high-pressure homogenizers, Ultra-Turrax apparatus and static mixers, for example systems having mixing nozzles.

In the context of the present invention, aqueous media are to be understood as meaning liquid media comprising water as main component, for example at least 60% by weight, preferably at least 80% by weight and especially at least 90% by weight. As further components, the aqueous medium may also comprise surfactants as described above. Moreover, the aqueous medium may already comprise a part or the total amount of the monomers M1 to be polymerized in step b). In a preferred embodiment, water is the only volatile component of the aqueous medium.

The amount of aqueous medium is preferably chosen such that the weight ratio mixture of active compound particles and surfactant to aqueous medium is in the range from 2:1 to 1:20 and in particular from 1.1:1 to 1:10.

For suspending the active compound particles, pressure and temperature conditions are generally not critical; in general, conditions under which the active compound particles do not melt are chosen. Suitable are, for example, temperatures in the range from 5 to 100° C., preferably from 20 to 85° C., and pressures in the range from atmospheric pressure to 10 bar.

Alternatively, the aqueous suspensions of the active compound particles can be prepared by precipitation methods. Such precipitation methods generally comprise dissolving the active compound in a water-miscible solvent and then mixing the solution with water in the presence of the surfactant, giving a finely divided suspension of the water-insoluble active compound which additionally comprises the surfactant and the organic solvent. The organic solvent is then generally removed. Processes to achieve this were described for the preparation of aqueous dispersions of colorants and can be employed in an analogous manner to prepare the aqueous suspension of active compounds.

In the suspension obtained in step a), an emulsion polymerization of the monomer composition M1 is carried out, if appropriate after dilution with aqueous medium. Below, the monomers of the monomer composition M1 are also referred to as monomers M1. This give an aqueous dispersion of a water-insoluble polymer which is formed at least partially at the surface of the active compound particles.

Prior to the initiation of the polymerization, the content of active compound in the aqueous suspension is preferably adjusted in the range from 0.1 to 400 g/l, in particular in the range from 0.5 to 300 g/l and especially from 1 to 200 g/l, of suspension, if appropriate by dilution with aqueous medium.

According to the invention, the monomers M1 comprise at least 95% by weight, based on the total amount of the monomers M1, preferably at least 99% by weight and in particular at least 99.9% by weight, of neutral, monoethylenically unsaturated monomers M1.1 having a solubility in water of not more than 30 g/l at 25° C./1013 mbar. Under these conditions, the solubility in water of the monomers M1.1 is in particular from 0.01 to 20 g/l and especially from 0.1 to 10 g/l. Suitable monomers M1.1 comprise vinylaromatic monomers, such as styrene, α-methylstyrene, tert-butylstyrene and vinyltoluene, esters of α,β-monoethylenically unsaturated mono- and dicarboxylic acids having 3 to 8 and in particular 3 or 4 carbon atoms with $C_1$-$C_{10}$-alkanols or with $C_5$-$C_8$-cycloalkanols, in particular the esters of acrylic acid, of methacrylic acid, of crotonic acid, the diesters of maleic acid, of fumaric acid and of itaconic acid, and particularly preferred the esters of acrylic acid with $C_2$-$C_{10}$-alkanols (=$C_2$-$C_{10}$-alkyl acrylates), such as ethyl acrylate, n-butyl acrylate, isobutyl acrylate, tert-butyl acrylate, n-hexyl acrylate, 2-ethylhexyl acrylate and 3-propylheptyl acrylate, and the esters of methacrylic acid with $C_2$-$C_{10}$-alkanols, such as ethyl methacrylate, n-butyl methacrylate, isobutyl methacrylate, tert-butyl methacrylate, n-hexyl methacrylate and the like. Suitable monomers M1.1 are furthermore vinyl esters and allyl esters of aliphatic carboxylic acids having 3 to 10 carbon atoms, for example vinyl propionate, and also the vinyl esters of Versatic® acids (vinyl versatates), vinyl halides, such as vinyl chloride and vinylidene chloride, conjugated diolefins, such as butadiene and isoprene, and also $C_2$-$C_6$-olefins, such as ethylene, propene, 1-butene and n-hexene. Preferred monomers M1.1 are vinylaromatic monomers, $C_2$-$C_{10}$-alkyl acrylates, in particular $C_2$-$C_8$-alkyl acrylates, especially tert-butyl acrylate, and also $C_2$-$C_{10}$-alkyl methacrylates and in particular $C_2$-$C_4$-alkyl methacrylates. In particular, at least 70% by weight of the monomers M1.1 are selected from vinylaromatic monomers, in particular styrene, esters of methacrylic acid with $C_2$-$C_4$-alkanols and tert-butyl acrylate. Particularly preferred monomers M1.1 are vinylaromatic monomers, especially styrene, and mixtures of vinylaromatic monomers with the abovementioned $C_2$-$C_8$-alkyl acrylates and or $C_2$-$C_4$-alkyl methacrylates, in particular mixtures having a content of vinylaromatic compounds of at least 60% by weight, based on the total amount of the monomers M1.1.

Furthermore, the monomers M1 may also comprise up to 5% by weight, for example from 0.1 to 5% by weight, based on the total weight of the monomers M1, of one or more ethylenically unsaturated monomers M1.2 different from the monomers M1.1. Preferably, the proportion of the monomers M1.2 of the total amount of the monomers M1 is less than 1% by weight, in particular not more than 0.1% by weight. The monomers M1.2 may have 1 or more, for example 1, 2, 3 or 4, ethylenically unsaturated double bonds and are generally selected from the monomers mentioned under step c) as monomers M2.2.

It has been found to be advantageous to choose the monomers of the monomer composition M1 such that they correspond to a polymer 1 having a theoretical glass transition temperature according to Fox $T_g$(Fox) of at least 50° C. According to Fox (T. G. Fox, Bull. Am. Phys. Soc. (Ser. II) 1, 123 [1956] and Ullmanns Enzyklopädie der technischen Chemie [Ullmann's Encyclopedia of Technical Chemistry], Weinheim (1980), pp. 17-18), the following applies to the glass transition temperature of mixed polymers with no crosslinking or little crosslinking and large molar masses, with good approximation:

$$\frac{1}{T_g} = \frac{X^1}{T_g^1} + \frac{X^2}{T_g^2} + \ldots \frac{X^n}{T_g^n}$$

where $X^1, X^2, \ldots, X^n$ are the mass fractions of monomers 1, 2, ..., n and $T_g^1, T_g^2, \ldots, T_g^n$ are the glass transition temperatures, in degrees Kelvin, of the polymers constructed in each case of only one of the monomers 1, 2, ..., n. The latter are known, for example, from Ullmann's Encyclopedia of Industrial Chemistry, VCH, Weinheim, vol. A 21 (1992), p. 169 or from J. Brandrup, E. H. Immergut, Polymer Handbook 3rd ed., J. Wiley, New York 1989.

Besides this, the glass transition temperature $T_g$ is to be understood as meaning the "midpoint temperature" determined according to ASTM D 3418-82 by differential thermal analysis (DSC) (cf. Ullmann's Encyclopedia of Industrial Chemistry, 5th edition, volume A 21, VCH Weinheim 1992, p. 169, and also Zosel, Farbe and Lack 82 (1976), pp. 125-134, see also DIN 53765).

The polymerization of the monomers M1 is carried out using the method of an emulsion polymerization, i.e. the monomer M1 to be polymerized is present as an aqueous emulsion in the polymerization mixture.

To this end, the monomers M1 may be added neat or in the form of an aqueous emulsion to the suspension of the active compound. The monomers M1 may, prior to the start of the polymerization, be initially charged in the reactor, or they may be added in one or more portions or continuously under polymerization conditions. Preferably, the major amount of the monomers M1, in particular at least 80% and particularly preferably the total amount or virtually the total amount is initially charged in the polymerization vessel, and the polymerization is then initiated by addition of a polymerization initiator.

In step b), the monomers M1 are preferably employed in an amount such that the weight ratio of active compound to monomer M1 is in the range from 10:1 to 1:50, in particular 5:1 to 1:30 and particularly preferably in the range from 2:1 to 1:20.

Initiators suitable for the emulsion polymerization in step b) are the polymerization initiators suitable and customarily used for an emulsion polymerization which initiate radical polymerization of ethylenically unsaturated monomers. These include azo compounds, such as 2,2'-azobisisobutyronitrile, 2,2'-azobis(2-methylbutyronitrile), 2,2'-azobis[2-methyl-N-(2-hydroxyethyl)propionamide, 1,1'-azobis(1-cyclohexane-carbonitrile), 2,2'-azobis(2,4-dimethylvaleronitrile), 2,2'-azobis(N,N'-dimethylene-isobutyroamidine)dihydrochloride and 2,2'-azobis(2-amidinopropane)dihydrochloride, organic or inorganic peroxides, such as diacetyl peroxide, di-tert-butyl peroxide, diamyl peroxide, dioctanoyl peroxide, didecanoyl peroxide, dilauroyl peroxide, dibenzoyl peroxide, bis(o-toluoyl) peroxide, succinyl peroxide, tert-butyl peracetate, tert-butyl permaleinate, tert-butyl perisobutyrate, tert-butyl perpivalate, tert-butyl peroctoate, tert-butyl perneodecanoate, tert-butyl perbenzoate, tert-butyl peroxide, tert-butyl hydroperoxide, cumene hydroperoxide, tert-butyl peroxy-2-ethylhexanoate and diisopropyl peroxydicarbamate, salts of peroxodisulfuric acid and redox initiator systems.

For the polymerization in step b), preference is given to using a redox initiator system, in particular a redox initiator system which comprises, as oxidizing agent, a salt of peroxodisulfuric acid, hydrogen peroxide or an organic peroxide, such as tert-butyl hydroperoxide. As reducing agent, the redox initiator systems preferably comprise a sulfur compound selected, in particular, from the group consisting of sodium bisulfite, sodium hydroxymethanesulfinate and the adduct of hydrogen sulfite and acetone. Other suitable reducing agents are phosphorus-containing compounds, such as phosphoric acid, hypophosphites and phosphinates, and also hydrazine or hydrazine hydrate and ascorbic acid. Redox initiator systems may also comprise small added amounts of redox metal salts, such as iron salts, vanadium salts, copper salts, chromium salts or manganese salts, such as, for example, the redox initiator system ascorbic acid/iron(II) sulfate/sodium peroxodisulfate. Particularly preferred redox initiator systems are acetone bisulfite adduct/organic hydroperoxide, such as tert-butyl hydroperoxide; sodium disulfite ($Na_2S_2O_5$)/organic hydroperoxide, such as tert-butyl hydroperoxide; sodium hydroxymethanesulfinate/organic hydroperoxide, such as tert-butyl hydroperoxide; and ascorbic acid/hydrogen peroxide.

The initiator is usually employed in an amount of from 0.02 to 2% by weight and in particular from 0.05 to 1.5% by weight, based on the amounts of the monomers M1. The optimum amount of initiator depends of course on the initiator system used and can be determined by the person skilled in the art in standard experiments. Some or all of the initiator may be initially charged in the reaction vessel.

For carrying out the polymerization of the monomers M1, pressure and temperature are of minor importance. Of course, the temperature depends on the initiator system used, and a person skilled in the art is able to determine an optimum polymerization temperature by standard experiments. The polymerization temperature is usually in the range from 0 to 110° C., frequently in the range from 30 to 95° C. Advantageously, the chosen polymerization temperature is a temperature in which the active compound is present as a solid. The polymerization is usually carried out at atmospheric pressure. However, it can also be carried out at elevated pressure, for example up to 10 bar, or at slightly reduced pressure, for example >800 mbar. The polymerization time in step b) is preferably 1 to 120 minutes, in particular 2 to 90 minutes and particularly preferably 3 to 60 minutes, longer or shorter polymerization times also being possible.

In step b), the polymerization is preferably carried out under starved conditions, i.e. conditions which permit little if any formation of empty micelles and thus the formation of active compound-free polymer particles. To this end, either no further surfactant is added, or the amount of further added surfactant is so small that the active compound particles are wetted by the water-insoluble monomers and stabilized in the aqueous phase. In this way, there are no measurable amounts of stabilized droplets of monomer M1 in which polymerization may take place present in the reaction mixture, and the surfactants present in the polymerization mixture serve essentially to wet the surface of the active compound particles and for the transport of monomer M1 across the continuous aqueous phase. Preferably, the amount of further surfactants added is not more than 5% by weight, for example 0.1 to 5% by weight, based on the monomers M1 to be polymerized. Suitable further surfactants are, in addition to the nonionic surfactants, in particular also anionic emulsifiers, for example alkyl sulfates, alkylsulfonates, alkylarylsulfonates, alkyl ether sulfates, alkylaryl ether sulfates, (di)alkylsulfosuccinates, such as sulfosuccinic acid monoesters and sulfosuccinic acid diesters, and alkyl ether phosphates, and furthermore the cationic emulsifiers mentioned in step c). Preferred further emulsifiers in step b) are the abovementioned anionic emulsifiers. In a preferred embodiment of the invention, the polymerization of the monomers M1 is carried out in the presence of such an anionic emulsifier.

It will be appreciated that further substances can be added to the polymerization mixture in step b) that are customary in emulsion polymerization, for example glycols, polyethylene glycols, buffers/pH regulators, molecular weight regulators and chain transfer inhibitors.

Step b) provides an aqueous polymer/active compound dispersion where the active compound particles of the active compound suspension initially prepared are coaked at least partially by the water-insoluble polymer formed by the monomers M1. No measurable amounts or only extremely small amounts of agglomerates are observed which are generally less than 2% by weight, preferably less than 0.2% by weight, based on the solids comprised in the dispersion.

A further step may be carried out whereby the dispersed polymer- or copolymer-coated active compound particles obtainable according to b) are isolated by purifying operations, for example filtering, decanting, washing, and redispersed for carrying out step c) of the process according to the invention. Preferably, however, the aqueous dispersion obtainable according to b) is processed further without further purification or isolation steps, i.e. in situ.

In step c) of the process according to the invention, an emulsion polymerization of the monomers M2 is carried out in an aqueous dispersion of the polymer/active compound particles obtained in step b).

According to the invention, the monomers M2 comprise at least 60% by weight, based on the total amount of the monomers M2, preferably at least 70% by weight and in particular at least 80% by weight of neutral monoethylenically unsaturated monomers M2.1 having a solubility in water of not more than 30 g/l at 25° C./1013 mbar. Suitable monomers are, in principle, all monomers mentioned as monomers M1.1, and also methyl methacrylate and vinyl acetate.

In a preferred embodiment of the present invention, the monomers M2.1 used in step c) comprise at least one monomer capable of swelling the polymer prepared in step b). Swelling is to be understood as meaning that, under normal conditions, at least 5% by weight of monomer M2.1 can be physically incorporated in the polymer of step b).

In a preferred embodiment of the invention, the monomers M2.1 are selected from vinylaromatic monomers and the abovementioned esters of α,β-ethylenically unsaturated $C_3$-$C_{10}$-mono- and -dicarboxylic acids with $C_1$-$C_{10}$-alkanols, including methyl methacrylate, or $C_3$-$C_{10}$-cycloalkanols. These are monomers which swell the polymer prepared in step b).

Furthermore, the monomers M2 may also comprise up to 40% by weight, for example from 0.5 to 40% by weight, in particular from 1 to 30% by weight, based on the total weight of the monomers M2, of one or more ethylenically unsaturated monomers M2.2 different from the monomers M2.1.

The monomers M2.2 include in particular monoethylenically unsaturated monomers M2.2a having at least one acid group or at least one anionic group, in particular monomers M2.2a having a sulfonic acid group, a phosphonic acid group or one or two carboxylic acid groups, and the salts of the monomers M2.2a, in particular the alkali metal salts, for example the sodium or potassium salts, and also the ammonium salts. These include ethylenically unsaturated sulfonic acids, in particular vinylsulfonic acid, 2-acrylamido-2-methylpropanesulfonic acid, 2-acryloxyethane-sulfonic acid and 2-methacryloxyethanesulfonic acid, 3-acryloxy- and 3-methacryloxypropanesulfonic acid, vinylbenzenesulfonic acid and salts thereof, ethylenically unsaturated phosphonic acids, such as vinylphosphonic acid and vinylphosphonic acid dimethyl ester and salts thereof, and α,β-ethylenically unsaturated $C_3$-$C_8$-mono- and $C_4$-$C_8$-dicarboxylic acids, in particular acrylic acid, methacrolic acid, crotonic acid, maleic acid, fumaric acid and itaconic acid. The proportion of the monomers M2.2a is frequently not more than 35% by weight, preferably not more than 20% by weight, for example from 0.1 to 20% by weight and in particular from 0.5 to 15% by weight, based on the total amount of the monomers M2.

The monomers M2.2 furthermore include the monoethylenically unsaturated neutral monomers M2.2b having a solubility in water of at least 50 g/l at 25° C. and in particular at least 100 g/l at 25° C. Examples of these are the amides of the abovementioned ethylenically unsaturated carboxylic acids, in particular acrylamide and methacrylamide, ethylenically unsaturated nitriles, such as methacrylonitrile and acrylonitrile, hydroxyalkyl esters of the abovementioned α,β-ethylenically unsaturated $C_3$-$C_8$-monocarboxylic acids and of the $C_4$-$C_8$-dicarboxylic acids, in particular hydroxyethyl acrylate, hydroxyethyl methacrylate, 2- and 3-hydroxypropyl acrylate, 2- and 3-hydroxypropyl methacrylate, esters of the abovementioned monoethylenically unsaturated mono- and dicarboxylic acids with $C_2$-$C_4$-polyalkylene glycols, in particular the esters of these carboxylic acids with polyethylene glycol or alkylpolyethylene glycols, where the (alkyl)polyethylene glycol radical usually has a molecular weight in the range from 100 to 3000. The monomers M2.2b furthermore include N-vinylamides, such as N-vinylformamide, N-vinylpyrrolidone, N-vinylimidazole and N-vinylcapro-lactam. The proportion of the monomers M2.2b is preferably not more than 20% by weight and in particular not more than 10% by weight, for example from 0.1 to 10 and in particular from 0.5 to 5% by weight, based on the total amount of the monomers M2.

The monomers M2.2 furthermore include monoethylenically unsaturated monomers M2.2c having at least one cationic group and/or at least one group which can be protonated in aqueous media. The monomers M2.2c include in particular those having a protonatable amino group, a quaternary ammonium group, a protonatable imino group or a quaternized imino group. Examples of monomers having a protonatable imino group are N-vinylimidazole and vinylpyridines. Examples of monomers having a quaternized imino group are N-alkylvinylpyridinium salts and N-alkyl-N'-vinylimidazolinium salts, such as N-methyl-N'-vinylimidazolinium chloride or methosulfate. Among the monomers M2.2c, particular preference is given to the monomers of the general formula I

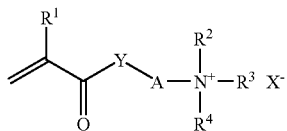

(I)

in which
$R^1$ is hydrogen or $C_1$-$C_4$-alkyl, in particular hydrogen or methyl,
$R^2$, $R^3$ independently of one another are $C_1$-$C_4$-alkyl, in particular methyl, and
$R^4$ is hydrogen or $C_1$-$C_4$-alkyl, in particular hydrogen or methyl,
Y is oxygen, NH or $NR^5$, where $R^5$=$C_1$-$C_4$-alkyl,
A is $C_2$-$C_8$-alkylene, for example 1,2-ethanediyl, 1,2- or 1,3-propanediyl, 1,4-butanediyl or 2-methyl-1,2-propanediyl which, if appropriate, is interrupted by 1, 2 or 3 non-adjacent oxygen atoms, and
$X^-$ is an anion equivalent, for example $Cl^-$, $HSO_4^-$, $½SO_4^{2-}$ or $CH_3OSO_3^-$, etc.,
and for $R^4$=H the free bases of the monomers of the formula I.

Examples of such monomers M2.2c are 2-(N,N-dimethylamino)ethylacrylate, 2-(N,N-dimethylamino)ethylmethacrylate, 2-(N,N-dimethylamino)ethylacrylamide, 3-(N,N-dimethylamino) propylacrylamide, 3-(N,N-dimethylamino)propylmethacrylamide, 2-(N,N-dimethylamino)ethylmethacrylamide, 2-(N,N,N-trimethylammonium)ethylacrylate chloride, 2-(N,N,N-trimethylammonium) ethylmethacrylate chloride, 2-(N,N,N-trimethylammonium) ethylmethacrylamide chloride, 3-(N,N,N-trimethylammonium)propylacrylamide chloride, 3-(N,N,N-trimethylammonium)propylmethacrylamide chloride, 2-(N,N,N-trimethylammonium)ethylacrylamide chloride, and the corresponding methosulfates and sulfates.

In a preferred embodiment, the polymer-forming monomers M2 comprise at least one monomer M2.2c. In this case, the proportion of the monomers M2.2c is advantageously from 0.1 to 20% by weight, in particular from 0.5 to 10% by weight and with particular preference from 1 to 7% by weight, based on the total amount of the monomers M2.

The monomers M2 furthermore include all monomers which can customarily be used in an emulsion polymerization. The proportion of monomers having two or more non-conjugated ethylenically unsaturated double bonds is, however, usually not more than 5% by weight, in particular not more than 2% by weight, for example from 0.01 to 2% by weight and in particular from 0.05 to 1.5% by weight, based on the total amount of the monomers M2.

Depending on the intended use, the monomers M2 may also comprise functional monomers, i.e. monomers which, in addition to a C=C double bond which can be polymerized, also have a reactive functional group, for example an oxirane group, a reactive carbonyl group, for example an acetoacetyl group, an isocyanate group, an N-hydroxymethyl group, an N-alkoxymethyl group, a trialkylsilyl group, a trialkoxysilyl group or another group reactive towards nucleophiles.

Furthermore, it has been found to be advantageous to choose the monomer composition M2 such that the resulting polymer has a glass transition temperature of at least 0° C., preferably at least 10° C., in particular in the range from 20 to 130° C.

The amount of monomer M2 is generally chosen such that the weight ratio of active compound to the total amount of the monomer mixtures M1 and M2 is in the range from 9:1 to 1:100, in particular from 5:1 to 1:40 and especially from 2:1 to 1:30.

Polymerization of the monomers M2 is carried out under conditions customary for an emulsion polymerization, i.e. in the presence of at least one customary polymerization initiator capable of initiating a free-radical polymerization of ethylenically unsaturated monomers. These include the polymerization initiators mentioned in step b). Preference is given to using water-soluble initiators, for example the water-soluble initiators mentioned in step b).

The initiator is usually employed in an amount of from 0.02 to 2% by weight and in particular from 0.05 to 1.5% by weight, based on the amount of the monomers M2. The optimum amount of initiator depends of course on the initiator system used and can be determined by the person skilled in the art in standard experiments. Some or all of the initiator may be initially charged in the reaction vessel. Preferably, the greater part of the initiator, in particular at least 80%, for example from 80 to 99.5%, of the initiator, is added to the polymerization reactor during the polymerization of the monomers M2.

The pressure and temperature are of minor importance for the polymerization of the monomers M2. The temperature depends of course on the initiator system used, and the person skilled in the art is capable of determining an optimum polymerization temperature by standard experiments. The polymerization temperature is usually in the range from 0 to 110° C., frequently in the range from 30 to 95° C. The polymerization is usually carried out at atmospheric pressure. However, it can also be carried out at elevated pressure, for example up to 10 bar, or at slightly reduced pressure, for example >800 mbar.

The polymerization in step c) is generally carried out according to a "monomer feed process", i.e. the greater part, preferably at least 70% and in particular at least 90%, of the monomers M2 is fed to the polymerization vessel in the course of the polymerization reaction. The addition of the monomers M2 can be in the form of an aqueous monomer emulsion of the monomers M2, or the monomers M2 are added neat to the polymerization reaction. The monomers M2 are preferably added over a period of at least 0.5 h, preferably at least 1 h, for example from 1 to 10 h and in particular from 1.5 to 5 h. The addition of the monomers M2 can be carried out at a constant or variable addition rate, for example in intervals at a constant addition rate or at a variable addition rate or continuously at a variable addition rate. During the addition, the composition of the monomer composition M2 can remain constant or can be changed.

In one embodiment of the invention, the monomer composition M2 is changed in the course of the monomer addition in such a way that polymer regions having a different glass transition temperature are obtained in the polymer particles. This is achieved by a "step polymerization". For this, first, a first monomer composition 2, the monomer composition of which corresponds to a glass transition temperature $T_G^1$, is polymerized in a first step, and subsequently a second monomer composition 2 which corresponds to a glass transition temperature $T_G^2$ (2nd step) and, if appropriate, subsequent thereto, successively one or more further monomer compositions 2, each corresponding to a glass transition temperature $T_G^n$, where n is the respective step, is/are added. The respective glass transition temperatures in polymers obtained in successive polymerization steps preferably differ by at least 10 K, in particular by at least 20 K and particularly preferably by at least 30 K, for example from 30 K to 200 K, in particular from 40 K to 160 K. Generally, the monomer amount polymerized in a step, based on the total amount of the monomers M2, will be at least 5% by weight, preferably at least 10% by weight, for example from 5 to 95% by weight, in particular from 10 to 90% by weight, in the case of a 2-step polymerization, and from 5 to 90 or from 5 to 85% by weight, in particular from 10 to 80% by weight, in the case of a polymerization of three steps or more.

It is preferred to add a further amount of at least one surfactant during the polymerization of the monomers M2. The further amount of surfactant is usually in the range from 0.1 to 10% by weight, based on the total amount of the monomers M2.

Suitable further surfactants in step c) are the emulsifiers and protective colloids usually employed for emulsion polymerization. These include the nonionic surfactants mentioned above in connection with step a), and furthermore anionic emulsifiers, anionic protective colloids, cationic emulsifiers, cationic protective colloids and zwitterionic (betainic) emulsifiers.

The amounts of surfactants usually employed for the emulsion polymerization in step c) are generally in the ranges given above, so that all or a portion of the surfactants in the compositions according to the invention is supplied via the emulsion polymerization. However, it is also possible to use, in the emulsion polymerization, only a portion, for example from 10 to 90% by weight, in particular from 20 to 80% by weight, of the surfactants present in the composition according to the invention and to add the remainder of the surfactants subsequent to the emulsion polymerization, before or after an optional deodorization of the emulsion polymerization (subsequent saponification).

Examples of anionic surfactants suitable for step c) include anionic emulsifiers, such as alkylphenylsulfonates, phenylsulfonates, alkyl sulfates, alkylsulfonates, alkyl ether sulfates, alkylphenol ether sulfates, alkylpolyglycol ether phosphates, alkyldiphenyl ether sulfonates, polyarylphenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, including their alkali metal, alkaline earth metal, ammonium and amine salts. Examples of anionic protective colloids are lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, and also polycarboxylates, such as polyacrylates, maleic anhydride/olefin copolymers (for example Sokalan® CP9, BASF), and also the alkali metal, alkaline earth metal, ammonium and amine salts of the abovementioned protective colloids.

Examples of cationic emulsifiers suitable for step c) include quaternary ammonium salts, for example trimethyl- and triethyl-$C_6$-$C_{30}$-alkylammonium salts, such as cocotrimethylammonium salts, trimethylcetylammonium salts, dimethyl- and diethyl-di-$C_4$-$C_{20}$-alkylammonium salts, such as didecyldimethylammonium salts and dicocodimethylammonium salts, methyl- and ethyl-tri-$C_4$-$C_{20}$-alkylammonium salts, such as methyltrioctylammonium salts, $C_1$-$C_{20}$-alkyl-di-$C_1$-$C_4$-alkylbenzylammonium salts, such as triethylbenzylammonium salts and cocobenzyldimethylammonium salts, methyl- and ethyl-di-$C_4$-$C_{20}$-alkylpoly(oxyethyl)ammonium salts, for example didecylmethylpoly(oxyethyl)ammonium salts, N—$C_6$-$C_{20}$-alkylpyridinium salts, for example N-laurylpyridinium salts, N-methyl- and N-ethyl-N—$C_6$-$C_{20}$-alkylmorpholinium salts, and also N-methyl- and N-ethyl-N'—$C_6$-$C_{20}$-alkylimidazolinium salts, in particular the halides, borates, carbonates, formates, acetates, propionates, bicarbonates, sulfates and methosulfates.

Examples of cationic protective colloids suitable for step c) include homo- and copolymers of the abovementioned monomers M2c having a content of monomers M2.2c of at least 20% by weight, in particular at least 30% by weight of monomers M2.2c, for example homopolymers of N-vinyl-N-methylimidazolinium salts or of N-alkylvinylpyridinium salts, and also copolymers of these monomers with neutral monomers M2.2b which are preferably miscible with water.

Zwitterionic emulsifiers are those having betainic structures. Such substances are known to the person skilled in the art and can be taken from the relevant state of the art (see, for example, R. Heusch, in Ullmann's Encyclopedia of Industrial Chemistry, 5th ed., on CD-ROM, Wiley-VCH 1997, "Emulsions", chapter 7, table 4).

The molecular weight of the polymers in step c) can obviously be adjusted by addition of a small amount of regulators, for example from 0.01 to 2% by weight, based on the monomers M which are being polymerized. Suitable regulators are in particular organic thio compounds, and also allyl alcohols and aldehydes.

Subsequent to the actual polymerization reaction in step c), it may be advantageous to substantially free the aqueous polymer/active compound compositions obtained from odorous substances, such as residual monomers and other volatile organic compounds. In a manner known per se, this can be achieved physically by distillative removal (in particular via steam distillation) or by stripping with an inert gas. Furthermore, the residual monomers can be lowered chemically by radical postpolymerization, in particular under the effects of redox initiator systems, such as are listed, for example in DE-A 44 35 423, DE-A 44 19 518 and DE A 44 35 422. The postpolymerization is preferably carried out with a redox initiator system comprising at least one organic peroxide and one organic sulfite.

After the end of the polymerization in step c), the aqueous polymer/active compound compositions obtained are frequently, before their use according to the invention, adjusted to an alkaline value, preferably to pH values ranging from 7 to 10. Ammonia or organic amines, and also, preferably, hydroxides, such as sodium hydroxide, potassium hydroxide or calcium hydroxide, can be used for the neutralization.

In this manner, stable aqueous active compound compositions are obtained which comprise at least one active compound in particulate form. The greater part of the active compound particles is coated with at least one layer of polymers or copolymers derived from monomers M1 and monomers M2. Most of the active compound particles in the active compound composition obtainable according to the invention are coated by two layers of polymers or copolymers, it being possible for the layers to interpene-trate and not having to be strictly separate from one another. Here and below, the particles characterized in this manner are also referred to as active compound-comprising polymer particles.

The invention thus provides the aqueous active compound composition obtainable by the process according to the invention.

The active compound compositions according to the invention have a number of advantages. Firstly, they are stable aqueous formulations of active compounds which are not or only poorly soluble in water. In particular, phase separation problems observed with conventional formulations and with micro- or nanodispersions of the active compounds and sedimentation of the active compound are not observed, even when drastic conditions are applied as encountered during the processes used for impregnating wood with fungicidally active compounds. When added in customary amounts, the content of volatile organic compounds is lower than in the case of comparable conventional formulations and compared to micro- or nanodispersions of active compounds. At the same time, the proportion of emulsifier is lower. Compared to other active compound formulations, there is significantly reduced leaching of the active compound from treated materials when exposed to water. Furthermore, interactions of the active compounds with other formulation components or other active compounds, which are frequently encountered with conventional formulations, are not observed. Additionally, degradation of the active compounds by substrate or environmental effects such as the pH of the medium or UV radiation is reduced or even prevented.

Surprisingly, a reduced activity of the active compound owing to the coating with a polymer is not observed. In contrast, the aqueous active compound compositions obtainable according to the invention are distinguished by an activity against the harmful organisms to be controlled which is at least comparable to the activity of conventional active compound preparations. Frequently, it is even possible to obtain better activities, so that, compared to conventional dispersions, the amount of active compound employed can be reduced.

In a preferred embodiment of the invention, the aqueous active compound compositions according to the invention comprise not more than 1% by weight, in particular not more than 0.1% by weight and especially not more than 500 ppm, based on the total weight of the composition, of volatile organic compounds. Here and below, volatile compounds are all organic compounds which, at atmospheric pressure, have a boiling point below 200° C.

As a result of the way in which they are produced, the aqueous active compound compositions according to the invention comprise surfactants. The total amount of surfactant in the composition is usually in the range from 0.1 to 20% by weight, in particular from 0.5 to 15% by weight and particularly preferably in the range from 1 to 10% by weight, based on the total amount of active compound and polymer.

In a first approximation, the solids content of the compositions according to the invention is determined by the active compound and the polymer and is generally in the range from 10 to 60% by weight and in particular in the range from 20 to 50% by weight.

The content of active compound in the compositions according to the invention is usually in the range from 0.1 to 30% by weight, preferably in the range from 0.5 to 20% by weight, based on the total weight of the composition.

The aqueous compositions according to the invention usually have a low viscosity, i.e. their viscosity according to Brookfield at 25° C. is generally not more than 1000 mPa·s and is in particular in the range from 10 to 200 mPa·s.

The active compound compositions thus obtainable can be used directly as such or after dilution. Moreover, the compositions according to the invention may also comprise customary additives, for example viscosity-modifying additives (thickeners), antifoams, bactericides and antifreeze agents.

Suitable thickeners are compounds which confer a pseudoplastic flow behavior to the formulation, i.e. high viscosity at rest and low viscosity in the agitated stage. Mention may be made, in this connection, for example, of customary thickeners based on polysaccharides, such as Xanthan Gum® (Kelzan® from Kelco), Rhodopol® 23 (Rhone Poulenc) or Veegum® (from R. T. Vanderbilt), and organically modified phyllosilicates, such as Attaclay® (from Engelhardt), Xanthan Gum® being preferred.

Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof.

Bactericides can be added to stabilize the compositions according to the invention against attack by microorganisms. Suitable bactericides are, for example, those based on isothiazolones such as the products sold under the commercial names Proxel® from Avecia (or Arch) or Acticide® RS from Thor Chemie and Kathon® MK from Rohm & Haas.

Suitable antifreeze agents are organic polyols, for example ethylene glycol, propylene glycol or glycerol. These are usually employed in amounts of not more than 10% by weight, based on the total weight of the active compound composition.

If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

In addition, the aqueous active compound compositions according to the invention can be formulated with conventional binders, for example aqueous polymer dispersions, water-soluble resins, for example water-soluble alkyd resins, or waxes.

The compositions according to the invention may also be formulated with conventional aqueous active compound compositions of the same active compound or a different active compound. A frequent result is an improvement of the stability of the conventional aqueous active compound composition.

The aqueous active compound compositions according to the invention can, after or in particular before a formulation with additives, be converted by customary drying methods, in particular by spray-drying or freeze-drying, into pulverulent active compound compositions. Accordingly, the invention also provides such pulverulent active compound compositions.

Before drying, a drying or spray auxiliary is preferably added to the aqueous active compound compositions according to the invention. Drying or spray auxiliaries for drying aqueous polymer dispersions are known. These include, in particular, the abovementioned protective colloids, for example polyvinyl alcohol, preferably having a degree of hydrolysis of >70%, carboxylated polyvinyl alcohol, phenolsulfonic acid/formaldehyde condensates, phenolsulfonic acid/urea/formaldehyde condensates, naphthalenesulfonic acid/formaldehyde condensates, naphthalenesulfonic acid/form-aldehyde/urea condensates, polyvinylpyrrolidone, maleic acid (anhydride)/styrene copolymers and ethoxylated derivatives thereof, copolymers of maleic anhydride with $C_2$-$C_{10}$-olefins such as diisobutene, and ethoxylated derivatives thereof, cationic polymers, for example homo- and copolymers of N-alkyl-N-vinylimidazolinium compounds with N-vinyllactams and the like, and also inorganic antiblocking agents, such as silicic acid, alumina and the like. The drying auxiliaries are usually employed in an amount of from 0.1 to 20% by weight, based on the mass of the active compound particles in the aqueous active compound composition.

The pulverulent active compound compositions obtained in this manner are usually redispersible in water and have the same advantages as the aqueous active compound compositions. The pulverulent active compound compositions according to the invention are, like the aqueous active compound compositions, suitable for crop protection and the protection of materials, so that what is said below with regard to the use of the aqueous active compound compositions according to the invention applies correspondingly also to the pulverulent active compound compositions according to the invention. Here, the pulverulent compositions according to the invention may, depending on the area of use, be applied as such, in the form of aqueous resuspended formulations or together with a solid carrier. Solid carriers include, for example, mineral earths, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

The active compound compositions according to the invention are suitable for numerous applications, and the active compound comprised in the composition is selected primarily with a view to the desired application.

In principle, the compositions according to the invention can be used in all areas of crop protection and of the protection of materials for controlling harmful organisms or for promoting plant growth. If the compositions according to the invention comprise a herbicide, they may be used analogously to known formulations of herbicidally active compounds for controlling harmful plants, in particular harmful grasses. If the compositions according to the invention comprise a fungicidally active compound, they can be used for controlling harmful fungi in crop protection and in the protection of materials. If the compositions according to the invention comprise an insecticide, acaricide or nematicide, they can be employed both for protecting plants and for protecting materials against attack by such animal pests. It is also possible to treat plants and materials that have been attacked with the compositions according to the invention and to destroy the damaging organisms or at least to inhibit their growth, so that they cause no damage. This applies correspondingly to compositions according to the invention comprising algicides, bactericides or other biocides. In a manner known per se, the type of active compound in the composition will depend on the harmful organism to be controlled.

Active compound compositions according to the invention comprising a fungicide, a bactericide, another biocide and/or an insecticide are particularly suitable in the different areas of the protection of materials against attack by harmful fungi or animal pests. Using the compositions according to the invention, it is possible, for example, to protect cellulose-containing materials, such as wood, and also skins, hides, leather, textiles, nonwovens and the like effectively against attack by microorganisms, in particular against attack by the abovementioned harmful fungi, bacteria, other microorganisms and/or against attack by animal pests. The compositions according to the invention may furthermore also be used as antifouling paints, for example in shipbuilding, or as algicidal paint systems for the fronts of buildings and roof tiles, depending in each case on the active compound they comprise. Moreover, the compositions according to the invention may be used as can and film preservatives. Accordingly, a preferred embodiment of the invention relates to those active compound compositions comprising, as active compound, at least one fungicide and/or insecticide.

The active compound compositions according to the invention comprising, as active compound, at least one fungicide and/or insecticide are particularly suitable for protecting cellulose-containing materials against attack by harmful organisms, in particular for the preservation of wood.

With a view to the use of the compositions according to the invention for protecting cellulose-containing materials against attack by microorganisms relevant in wood preservation-especially mould fungi, wood-discoloring and wood-destroying fungi-preference is given in particular to fungicides effective, for example, against the following groups of microorganisms:

Wood-Discoloring Fungi:

Ascomycetes, such as *Ophiostoma* sp. (for example *Ophiostoma piceae, Ophiostoma piliferum*), *Ceratocystis* sp. (for example *Ceratocystis coerulescens*), *Aureobasidium pullulans, Sclerophoma* sp. (for example *Sclerophoma pityophila*);

Deuteromycetes, such as *Aspergillus* sp. (for example *Aspergillus niger*), *Cladosporium* sp. (for example *Cladosporium sphaerospermum*), *Penicillium* sp. (for example *Penicillium funiculosum*), *Trichoderma* sp. (for example *Trichoderma viride*), *Alternaria* sp. (for example *Alternaria alternata*), *Paecilomyces* sp. (for example *Paecilomyces variotii*);

Zygomycetes, such as *Mucor* sp. (for example *Mucor hiemalis*);

Wood-Destroying Fungi:
Ascomycetes, such as *Chaetomium* sp. (for example *Chaetomium globosum*), *Humicola* sp. (for example *Humicola grisea*), *Petriella* sp. (for example *Petriella setifera*), *Trichurus* sp. (for example *Trichurus spiralis*);
Basidiomycetes, such as *Coniophora* sp. (for example *Coniophora puteana*), *Coriolus* sp. (for example *Coriolus versicolor*), *Gloeophyllum* sp. (for example *Gloeophyllum trabeum*), *Lentinus* sp. (for example *Lentinus lepideus*), *Pleurotus* sp. (for example *Pleurotus ostreatus*), *Poria* sp. (for example *Poria placenta, Poria vaillantii*), *Serpula* sp. (for example *Serpula lacrymans*) and *Tyromyces* sp. (for example *Tyromyces palustris*), Accordingly, preferred active compounds are selected from the group of the conazoles, the group of the strobilurins, the group of the thiazoles, the group of the sulfenamides and the group of the iodine compounds.

Preference is given in particular to those fungicides mentioned in category 08 (wood preservatives) in the biocide regulation of the European Union (COMMISSION REGULATION (EC) No. 2032/2003 of Nov. 4, 2003).

With a view to the use of the compositions according to the invention for protecting cellulose-containing materials against attack by animal pests relevant in the preservation of wood, preference is given to those insecticides which are effective against wood-destroying insects and in particular against the following wood-destroying insects:

Order Coleoptera (Beetles):
   Cerambycidae, such as *Hylotrupes bajulus, Callidium violaceum;*
   Lyctidae, such as *Lyctus linearis, Lyctus brunneus;*
   Bostrichidae, such as *Dinoderus minutus;*
   Anobiidae, such as *Anobium punctatum, Xestobium rufovillosum;*
   Lymexylidae, such as *Lymexylon navale;*
   Platypodidae, such as *Platypus cylindrus;*
   Oedemeridae, such as *Nacerda melanura.*
Order Hymenoptera:
   Formicidae, such as *Camponotus abdominalis, Lasius flavus, Lasius brunneus, Lasius fuliginosus;*
Order Isoptera (Termites):
   Calotermitidae, such as *Calotermes flavicollis, Cryptothermes brevis;*
   Hodotermitidae, such as *Zootermopsis angusticollis, Zootermopsis nevadensis;*
   Rhinotermitidae, such as *Reticulitermes flavipes, Reticulitermes lucifugus, Coptotermes formosanus, Coptotermes acinaciformis;*
   Mastotermitidae, such as *Mastotermes darwiniensis.*

These include in particular the insecticidally active compounds from the class of the pyrethroids, arthropod growth regulators, such as chitin biosynthesis inhibitors, ecdysone antagonists, juvenoids, lipid biosynthesis inhibitors, neonicotinoids, pyrazole insecticides, and also chlorfenapyr. Accordingly, preferred embodiments relate to active compound compositions according to the invention comprising at least one of the insecticidally active compounds mentioned above.

Preference is given in particular to those insecticidally active compounds mentioned in category 08 (wood preservatives) and category 18 (insecticides, acaricides and products to control other arthropods) in the biocide regulation of the European Union (COMMISSION REGULATION (EC) No. 2032/2003 of Nov. 4, 2003).

For wood preservation, the active compound compositions according to the invention may also be formulated with classic water-soluble wood preservatives, in particular with their aqueous solutions, to improve the overall activity against wood-destroying organisms. These are, for example, aqueous preparations of conventional wood preservative salts, for example of salts based on boric acid and alkali metal borates, based on quaternary ammonium compounds, for example trimethyl- and triethyl-$C_6$-$C_{30}$-alkylammonium salts, such as cocotrimethylammonium chloride, trimethylcetylammonium salts, dimethyl- and diethyl-di-$C_4$-$C_{20}$-alkylammonium salts, such as didecyldimethylammonium chloride and bromide, dicocodimethylammonium chloride, $C_1$-$C_{20}$-alkyl-di-$C_1$-$C_4$-alkylbenzylammonium salts, such as cocobenzyldimethylammonium chloride, methyl- and ethyl-di-$C_4$-$C_{20}$-alkylpoly(oxyethyl)ammonium salts, for example didecylmethylpoly(oxyethyl)ammonium chloride and propionate, and the borates, carbonates, formates, acetates, bicarbonates, sulfates and methosulfates, aqueous preparations of copper/amine complexes, in particular aqueous preparations of copper ethanolamine-containing salts, for example Cu—HDO. The aqueous active compound compositions according to the invention may, of course, also be formulated with other aqueous herbicidal, fungicidal, insecticidal, acaricidal, nematicidal or other active compound formulations, for example with conventional emulsion concentrates, suspension concentrates, suspoemulsion concentrates of the abovementioned active compounds, for example the abovementioned fungicides from the group of the azoles and the strobilurins, or the abovementioned insecticides, or with the abovementioned microemulsions of the abovementioned fungicides and insecticides. By mixing the active compound composition according to the invention with conventional aqueous preparations of the abovementioned active compounds, firstly, the activity spectrum is widened when the conventional preparation comprises an active compound different from that in the active compound composition according to the invention. Secondly, the formulation with conventional aqueous active compound preparations does not result in a loss of the advantages of the active compound compositions according to the invention, in particular the improved adhesion to cellulose-containing materials and especially wood. It is thus possible to improve the application properties of a conventional aqueous active compound preparation by formulation with an active compound composition according to the invention of the same active compound.

The present invention also relates to a method for protecting cellulose-containing materials, in particular wood, against attack by harmful fungi, in particular against attack by the abovementioned wood-damaging fungi, by treating the cellulose-containing material, in particular wood, with a composition according to the invention.

Cellulose-containing materials are, in addition to wood and secondary wood products, for example wood cuttings, plywood, particle board, medium density fiber (MDF) board, oriented strand boards (OSB), furthermore pulp and intermediates in paper manufacture, fabrics based on cellulose, such as cotton, materials based on woody annual plants, for example shaped particles made of oilseed rape shavings, boards made of bargasse, boards made of straw, etc. The cellulose-containing materials furthermore include articles made of cellulose-containing fiber materials, such as fabrics, nonwovens, paper, cardboard, heat insulation materials, ropes, etc. Fiber materials suitable for the process according to the invention include textile fibers, such as flax, linen, hemp, jute, cotton and China grass, paper fibers, such as flax, linen, hemp, bamboo fibers, paper mulberry tree fibers and wood pulp, furthermore nettle fibers, Manila hemp, sisal, kenaf and coconut fiber.

Treatment can be carried out in a manner known per se, depending on the type of substrate by spraying, spreading, dipping or drenching the substrate with an undiluted or water-diluted active compound composition according to the invention or by flooding the substrate in an undiluted or water-diluted aqueous active compound composition according to the invention. The compositions according to the invention can also be present during the manufacture of the cellulose-containing material, for example as a binder or a glue.

If the substrate according to the invention is wood, it is possible to employ methods customary in wood preservation, as known, for example, from Ullmann's Encyclopedia of Industrial Chemistry, Wood preservation, 5th edition on CD-ROM, Wiley VCH, Weinheim, 1997, chapter 7. These include in particular methods for drenching the wood using differences in pressure, for example the boiler pressure process and double vacuum drenching.

The treatment of such materials with the active compound compositions according to the invention can be carried out using processes customary for this purpose and is in each case adapted in a manner known per se to the prevailing technical conditions. The application concentration and the introduction depends on how much the material is at risk and on the respective treatment process and is usually in the range from 0.05 mg to 10 g of active compound per kg of material.

For secondary wood products and cellulose-containing materials, the undiluted active compound-containing composition will frequently be employed, for example as a cobinder together with the binder used. Separate treatment during or after the preparation, for example gluing, is, of course, also possible.

The examples below are meant to illustrate the invention without limiting it:

The stated viscosities were determined in a rotation viscometer according to Brookfield similarly to ISO 2555 at 23° C.

The stated particle sizes were determined by dynamic light scattering by the methods described above using dilute dispersions (0.01 to 0.1% by weight strength). What is stated is the mean diameter determined by cumulant evaluation of the measured autocorrelation function.

The glass transition temperature was determined by differential calorimetry similarly to ASTM-D3418.

EXAMPLES

General Preparation Protocol a) Preparation of an aqueous suspension of active compound particles:

In a ball mill Drais Superflow DCP SF 12, the following components were ground together:

125 g of active compound
224.9 g of an aqueous 20% by weight strength solution of ethoxylated stearyl alcohol having a degree of ethoxylation of 25
0.1 g of distilled water Grinding was continued until the pigment particles had a mean diameter of 100 nm (owing to aggregate formation, the measured average particle diameter was initially 800-900 nm).

In a suitable reaction vessel, 25.7 g of the active compound preparation obtained in this manner were dispersed with stirring in 50 g of distilled water.

b) Polymerization of the monomers M1:

1.1 g of emulsifier solution 1 (40% by weight strength), 6 g of styrene (S), 2 drops of formic acid, 0.03 g of sodium hydroxymethanesulfinate and 0.04 g of a 70% by weight strength aqueous tert-butyl hydroxide solution were added to the active compound suspension prepared in step a), and the mixture was then heated to 85° C. and the temperature was maintained for 5 min.

c) Polymerization of the monomers M2:

5 minutes after the addition of tert-butyl hydroperoxide and sodium hydroxymethanesulfinate, an aqueous emulsion of the monomers M2 having a pH of 4 and the following composition:
40 g of demineralized water
2.3 g of a 40% by weight strength aqueous solution of ethoxylated oleylamine having a degree of ethoxylation of 11-12 (=emulsifier solution 1)
6.6 g of a 56.5% by weight aqueous solution of sodium (di-2-ethylhexylsuccinate)-sulfonate (sodium salt of sulfosuccinic acid di-2-ethylhexyl ester)
0.6 g of acrylic acid (AA)
2.7 g of dimethylaminopropylmethacrylamide (DMAPMAM)
13.8 g of methyl methacrylate (MMA)
4.5 of n-butyl acrylate (n-BA)
8.4 g of ethyl acrylate (EA) and
about 1 ml of formic acid
was added over a period of 60 minutes.

At the same time, over a period of 75 min, a solution of 0.6 g of azobisisobutyramidine dihydrochloride in 25 g of water was added, and the mixture was, after the addition had ended, stirred for a further 15 min whilst maintaining the temperature.

This gave an aqueous epoxiconazole-comprising dispersion. The solids content was 23.9% by weight. The maximum of the particle size distribution of the active compound/polymer particles was at 127 nm (determined using an Autosizer IIC from Malvern according to ISO 13321). The polymer had a glass transition temperature of −1° C.

The dispersions of examples 2 to 6 listed in table 1 were prepared in an analogous manner:

TABLE 1

| Example | Active compound (polymer/active compound)[1] | Monomers in step c) [pphm][2] | Particle size [nm] | SC[3] [% by weight] | Tg[4] [°C.] |
|---|---|---|---|---|---|
| 1 | epoxiconazole (4:1) | n-BA 15; MMA 46; EA 28; AA 2; DMAPMAM 9 | 127 | 23.9 | −1 |
| 2 | epoxiconazole (4:1) | MMA 95; DMAEMA 5 | 78 | 21.0 | 110 |
| 3 | chlorfenapyr (10:1) | BA: 15; MMA: 50; EA: 33; AA: 2; | 64 | 28.0 | 17 |
| 4 | chlorfenapyr (5:1) | BA: 15; MMA 50; EA 28; AA: 2; DMAPMAM 5 | 130 | 36.0 | 8 |

TABLE 1-continued

| Example | Active compound (polymer/active compound)[1] | Monomers in step c) [pphm][2] | Particle size [nm] | SC[3] [% by weight] | Tg[4] [°C.] |
|---|---|---|---|---|---|
| 5 | α-cypermethrin (4:1) | n-BA 15; MMA 46; EA 28; AA 2; DMAPMAM 9 | 127 | 23.9 | −1 |
| 6 | α-cypermethrin (3:1) | BA: 15; MMA: 50; EA: 33; AA: 2; | 64 | 28.0 | 17 |

[1] weight ratio of polymer to active compound
[2] stated in parts by weight per 100 parts by weight of total monomer; nBMA = n-butyl methacrylate, BA = n-butyl acrylate, EA = ethyl acrylate, AA = acrylic acid, DMAPMAM = 3-(dimethylamino)propylmethacrylamide, DMAEMA = 2-dimethylaminoethyl methacrylate.
[3] SC = solids content
[4] glass transition temperature Application Test:
Insecticidal Activity The insecticidal action of the compounds was demonstrated by the following test:

Using water, the aqueous active compound composition according to the invention from example 5 was diluted to three different active compound concentrations. For comparison, α-cypermethrin was dissolved in acetone, and the solution was diluted to the corresponding active compound concentrations using further acetone.

To determine the activity thresholds of the composition according to the invention against wood-destroying soil termites (Reticulitermes santonensis), wood samples from Pinus spp. of the dimensions 25×25×6 mm³ (Southern Yellow Pine), which met the American test standard AWPA E1-97 (see "Standard method for laboratory evaluation to determine resistance to subterranean termites", American Wood-Preservers' Association, 2001) were tested in a forced test after leaching stress according to DIN EN 84: 1997-01 (see "accelerated aging of treated wood prior to biological testings", European Committee for Standardization).

The destruction of the wood caused by the termite attack was, after a 4-week test period, evaluated by visual scoring of the sample woods in accordance with AWPA E1-97. In addition, the mortality rate among the termites was estimated.

When the sample woods were still intact (a score of 10 "sound, surface nibbles permitted" on a scale from 10 to 0), the protection of the wood achieved by the preservative at a certain active compound concentration was considered to be sufficient.

For the aqueous active compound composition according to the invention, the threshold for α-cypermethrin after leaching was determined to be 9-21 g/m³. Here, the lower concentration indicates the value at which the wood is no longer sufficiently protected (in the present case a score of 7 "moderate attack, penetration"), and the higher concentration corresponds to the minimum concentration providing complete protection. For the active compound which had been dissolved in pure acetone for comparison, the threshold after leaching was above 21 g/m³.

Fungicidal Activity

The activity threshold of the composition according to the invention from example 1 against wood-destroying Basidiomycetes was determined by the agar block method on wood samples from Pinus spp. (Southern Yellow Pine) of the dimensions 40×15×4 mm³. The test method with wood samples reduced in size, known as bravery test, is very similar to EN 113 and serves to determine the prophylactic action of wood preservatives against wood-destroying fungi (see A. F. Bravery, Intern. Res. Group Wood Pres., Doc. No. IRG/WP/ 2113, 5S., Stockholm 1978). For comparison, a solution of epoxiconazole in acetone was tested under the same conditions.

The wood samples impregnated with the composition according to the invention were, with and without leaching stress, tested according to EN 84. The test was carried out using four different active compound concentrations and in each case 5 parallel samples per active compound concentration and test fungus. The test fungi used were Coniophora puteana BAM Ebw. 15, Poria placenta FPRL 280 and Coriolus versicolor CTB 863A. The destruction of the wood caused by the fungal attack was evaluated using the weight loss of the sample woods, which was determined after 6 weeks. If the weight loss is less than 3% by weight, based on the initial dry weight of the test sample, the protection of the wood achieved by the preservative at a certain active compound concentration is considered to be sufficient. The activity concentration threshold is stated in two concentrations. The lower concentration indicates the value at which the wood is no longer sufficiently protected and the higher concentration corresponds to the minimum concentration required for complete protection.

The activity thresholds are shown in table 2. The values determined for a solution of the active compound in acetone are shown for comparison.

TABLE 2

| | Activity thresholds [g/m³] | |
|---|---|---|
| Test fungus | without leaching | with leaching |
| Dispersion with epoxiconazole* | | |
| C. puteana | >41 | >41 |
| P. placenta | 41-66 | 41-66 |
| C. versicolor | >41 | >41 |
| Solution of epoxiconazole** | | |
| C. puteana | <190 | 110-160 |
| P. placenta | <190 | 110-180 |

*Example 1
**A Solution in acetone

Important for the evaluation of a wood preservative in practice is in particular the upper value after leaching. The results shown in table 2 demonstrate that the active compound composition according to the invention has better activity against wood-destroying fungi than the formulation in organic solvent.

The invention claimed is:

1. A process for preparing an aqueous active compound composition for the protection of crops or materials, which process comprises the following steps:

a) providing an aqueous suspension of (1) solid active compound particles of at least one active compound having a solubility in water of not more than 5 g/l at 25° C./1013 mbar, and at least one surfactant, wherein the active compound particles in the suspension have a mean particle size, determined by dynamic light scattering, of 20 to 1200 nm, where the preparation of the suspension of the solid active compound particles comprises comminution of the solid active compound in the presence of the at least surfactant, or precipitating the active compound from a solution of the active compound in the presence of the at least one surfactant, b) adding a first monomer composition M1 to the suspension of solid active compound particles and initiating an emulsion polymerization of said first monomer composition M1 in the aqueous suspension of the active compound, wherein the monomer composition M1 comprises at least 95% by weight, based on its total weight, of at least one neutral, monoethylenically unsaturated monomer M1.1 having a solubility in water of not more than 30 g/l at 25° C./1 013 mbar, giving an aqueous dispersion of polymer/active compound particles, and c) conducting emulsion polymerization of a second monomer composition M2 in an aqueous dispersion of the polymer/active compound particles obtained in step b), wherein the monomer composition M2 comprises at least 60% by weight, based on its total weight, of at least one neutral, monoethylenically unsaturated monomer M2.1 having a solubility in water of not more than 30 g/l at 25° C./1013 mbar, wherein the monomer M1.1 is selected from the group consisting of vinylaromatic monomers and the esters of $\alpha,\beta$-ethylenically unsaturated mono- and dicarboxylic acids having 3 to 8 carbon atoms with $C_1$-$C_{10}$-alkanols or $C_3$-$C_{10}$-cycloalkanols, wherein the monomer M2.1 is selected from the group consisting of vinylaromatic monomers and the esters of $\alpha,\beta$-ethylenically unsaturated $C_3$-$C_{10}$-monocarboxylic and $C_3$-$C_{10}$-dicarboxylic acids with $C_1$-$C_{10}$-alkanols or $C_3$-$C_{10}$-cycloalkanols, and wherein the active compound is a solid at a temperature of 50° C. and selected from the group consisting of herbicides, fungicides, insecticides, acaricides, nematicides, bactericides, algicides, molluscicides, plant growth regulators and biocides.

2. The process according to claim 1, wherein the aqueous suspension of solid active compound particles comprises at least one nonionic surfactant.

3. The process according to claim 2, wherein the weight ratio of nonionic surfactant to active compound is in the range from 2:1 to 1:50.

4. The process according to claim 1, wherein the suspension of the solid active compound particles in step a) is provided by comminuting solid active compound in a mixture of the active compound with the surfactant and then dispersing the mixture obtained in this manner in an aqueous medium.

5. The process according to claim 1, wherein the monomer composition M1 corresponds to a polymer 1 having a theoretical glass transition temperature according to Fox $T_g$ of 30 to 180° C.

6. The process according to claim 1, wherein at least 70% by weight of the monomers M1.1 are selected from the group consisting of vinylaromatic monomers, esters of methacrylic acid with $C_2$-$C_4$-alkanols and tert-butyl acrylate.

7. The process according to claim 1, wherein the weight ratio of active compound to the monomers in the monomer composition M1 is in the range from 10:1 to 1:50.

8. The process according to claim 1, wherein at least 70% by weight of the monomers M1 are initially charged in the aqueous suspension of the active compound and the polymerization is then initiated in the monomer/active compound emulsion obtained in this manner.

9. The process according to claim 1, wherein the polymerization in step b) is carried out in the presence of an anionic emulsifier.

10. The process according to claim 1, wherein the polymerization of the monomers M1 is initiated by a Redox initiator.

11. The process according to claim 1, wherein the weight ratio of the total amount of monomer mixtures M1 and M2 to active compound is in the range from 1:9 to 100:1.

12. The process according to claim 1, wherein the monomers M2 comprise at least one monomer M2.2 in an amount of from 0.5 to 40% by weight, based on the total amount of the monomers M2, which monomer M2.2 is selected from the group consisting of monoethylenically unsaturated monomers M2.2a having at least one acid group or at least one anionic group;

monoethylenically unsaturated neutral monomers M2.2b having a solubility in water of at least 50 g/l at 25° C.; and monoethylenically unsaturated monomers M2.2c having at least one cationic group and/or at least one group which can be protonated in aqueous medium.

13. The process according to claim 1, wherein the active compound is selected from the group consisting of conazole fungicides, strobilurins and arylpyrrols.

14. An aqueous active compound composition obtained by a process according to claim 1.

15. The active compound composition according to claim 14, wherein the active compound is present in an amount of from 0.5 to 30% by weight, based on the total weight of the composition.

16. The active compound composition according to claim 14 comprising at least one fungicidally active compound.

17. The active compound composition according to claim 14 comprising at least one insecticidally active compound.

18. A method for protecting materials against infestation by harmful organisms and for treating materials infested by a harmful organism which comprises treating the material with an active compound composition according to claim 14, wherein the composition comprises at least one active compound from the group consisting of insecticides, acaricides, algicides, biocides, bactericides and fungicides.

19. The method as claimed in claim 18 for protecting wood against infestation by wood-damaging organisms.

20. A method for crop protection which comprises applying to a crop plant an active compound composition according to claim 14, wherein the active compound composition comprises at least one active compound from the group of the insecticides, acaricides, herbicides, plant growth regulators and fungicides.

* * * * *